(12) United States Patent
Xu et al.

(10) Patent No.: US 7,667,014 B2
(45) Date of Patent: Feb. 23, 2010

(54) METHOD OF DETECTING THE EXPRESSION OF PPN/MG61 AND THE USE OF IT

(75) Inventors: Junpu Xu, Beijing (CN); Xiaohua Qin, Beijing (CN)

(73) Assignee: Beijing ACCB Biotechltd, Beijing (CN)

( * ) Notice: Subject to any disclaimer, the term of this patent is extended or adjusted under 35 U.S.C. 154(b) by 183 days.

(21) Appl. No.: 11/675,636

(22) Filed: Feb. 16, 2007

(65) Prior Publication Data

US 2007/0269423 A1 Nov. 22, 2007

Related U.S. Application Data

(63) Continuation of application No. PCT/CN2005/001287, filed on Aug. 18, 2005.

(51) Int. Cl.
*C07H 21/02* (2006.01)

(52) U.S. Cl. .................................. 536/23.1; 536/24.3
(58) Field of Classification Search ................ 536/23.1, 536/24.3
See application file for complete search history.

(56) References Cited

OTHER PUBLICATIONS

Caricasole et al (Gene, 288:147-157, 2002).*
Chen et al (Oncogene:27,3483-3488, 2008).*

* cited by examiner

*Primary Examiner*—Stephen L Rawlings
*Assistant Examiner*—Brad Duffy
(74) *Attorney, Agent, or Firm*—George G. Wang; Bei & Ocean

(57) ABSTRACT

The present invention is directed to methods for comparatively detecting the level of human Porcupine (PPN)/MG61, a family member of membrane-bound O-acyltransferases, which is the human homologue of the *Drosophila* polarity gene Porcupine (Porc), and use thereof.

3 Claims, 22 Drawing Sheets

H1703

Control siRNA    PPN/MG61 siRNA

A549

Control siRNA     PPN/MG61 siRNA

Figure 13

```
HS   ACAT     410  STSYSNYY...RTWNVVVHDWLYYYAYKDFL........WFFSKRFKSAAMLAVFAVSAVVHEYALAVCLSFF
HS   ACAT2    384  STSFSNYY...RTWNVVVHDWLYSYVYQDGL........RLLGARARGVAMLGVFLVSAVAHEYIFCFVLGFF
MM   DGAT     378  AESVTYFW...QNWNIPVHKW.IRHFYKPML..........RHGSSKWVARTGVFLTSAFFHEYLVSVPLRMF
AT   DGAT     399  AKSVGDYW...RMWNMPVHKWMVRHIYFPCL..........RSKIPKTLAIIIAFLVSAVFHELCIAVPCRLF
SC   Are1     498  CVSFEEFS...RIWNVPVHKFLLRHVYHSSM..........GALHLSKSQATLFTFFLSAVFHEMAMFAIFRRV
SC   Are2     530  CVSWADFS...RIWNIPVHKFLLRHVYHSSM..........SSFKLNKSQATLMTFFLSSVVHELAMYVIFKKL
SI   WaxSyn   198  ATSLQDFW..GRRWNLMVSDILGLTTYQPVR...RVLSRWVRLRWEVAGAMLVAFTVSGLMHEVFFFYLTRAR
DM   Porc     346  PRSISSLV...RSWNIPMHEWLKRYIYAPCK......PTASTSRGRILVVVLSTYLVSSLLHGMDLRIYLVLI
CE   Mom-1    275  SRSTLQTV...SEWNKPFHTFLHENIFKRRL...........FNSTACNVFFTFAVSSLLHGLDFQMTITLL
HS   MG61     268  PRSMVEVV...TSWNLPMSYWLNNYVFKNAL...........RLGTFSAVLVTYAASALLHGFSFHLAAVLL
BS   dltB     270  SKNIKDFW...NRWHMSLSFWFRDYVFMRFVFWMTKKKWIKNRMAVSNIGYFLLFMLMGVWHGLAPQYIIYGL
SA   dltB     283  AKNIKDFW...NRWHMTLSFWFRDCIYMRSLFYMSRKKLLKSQFAMSNVAFLINFFIMGIWHGIEVYYIVYGL
PA   algI     271  SQSITEFW...RRWHISLSTWLRDYLYISLG.......GNRGSTFQTYRNLFLTMLLGGLWHGANFTYIIWGA
TP   algI     285  SQSVTEFW...RRWHISFSQWLKEYLYFSLG.........GSRFGIKRTVCALFFTMLIAGLWHGVRLTFLLWGM
SC   Ygl084c  400  NYSSLAFW...RAWHRSYNKWVVRYIYIPLG.........GSKNRVLTSLAVFSFVAIWHDIELKLLLWGW
SC   Ygl189W  449  NYSTVGFW...RAWHTSFNKWVIRYIYVPFG..........GSNNKILTSFAVFSFVAIWHDIQLRVLFWGW
SC   Yor175c  333  AQNTREML....AWNMNTNKWLKYSVYLRVT..........KKGKKPGFRSTLFTFLTSAFWHGTRPGYYLTFA
HS   BB1      180  CVRVRDGM...RYWNMTVQWWLAQYIYKSAP...........ARSYVLRTAWTMLLSAYWHGLHPGYYLSFL
DM   Nessy    311  GNTMEHYV...QSFNVNTNQWVGQYIYKRLK..........FLNNRTISYGAALGFLAVWHGYHSGYYMTFL
MM   C3F      277  FETTPRFNGTIASFNINTNAWVARYIFKRLK..........FLGNKELSQGLSLLFLALWHGLHSGYLICFQ
                    **  ***    * ***  *  **  ***  *           *  ** * *********** *  *** *
```

METHOD OF DETECTING THE EXPRESSION OF PPN/MG61 AND THE USE OF IT

CROSS REFERENCE TO RELATED APPLICATIONS

This application is a continuation application of PCT Application No. PCT/CN2005/001287, filed on Aug. 18, 2005, which claims priority to Chinese Patent Application No. 2004100700857, filed on Aug. 19, 2004, the content of which is hereby incorporated by reference.

FIELD OF THE INVENTION

The present invention provides a method for measuring the expression and activity level of PPN/MG61 in a human cell, treating cancer by inhibiting the enzyme activities and use thereof. More particularly, the present invention provides a method for comparatively measuring the expression and activity level of PPN/MG61 in a normal and cancer cell, treating cancer by inhibiting the enzyme activities and uses thereof.

BACKGROUND OF THE INVENTION

Wnt (wingless and int homologue) is a family of cysteine-rich secreted glycoproteins and has been identified in many vertebrates and invertebrates. They have been shown to have important roles for the decision of cell fate and behavior at multiple stages during development and cancer. They bind a family of specific receptors on the cell surface (Frizzled (Fz) family) and activate the cell signaling pathways to elicit their effects on, for example, gene transcription (Cadigan K M and Nusse R, 1997; Polakis P, 2000). One of the hallmarks of the Wnt family is the existence of 23 or 24 cysteine residues at conserved positions in the protein molecules. It has been assumed that these cysteine residues may have a critical role for folding of Wnt proteins by disulfide bond formation.

The processing and secretion of Wnt proteins was studied with cultured cells engineered to express various Wnts (Smolich B D, et al, 1993; Burrus L W and McMahon A P, 1995). The processing of Wnt is not efficient in most cell types, because multiple processing intermediates are present. Wnt is therefore not well secreted outside of the cells. Most of Wnt protein associates with a HSP70 protein, BiP, and is retained in the ER (Kitajewski J, et al, 1992). Screening for genes involved in Wg (*Drosophila* homologue) signaling by *Drosophila* deficiency kits has also identified a new gene(s), whose product(s) is required for the processing or secretion of Wg (Muller H, et al, 1999). These results indicate that the processing and secretion of Wnt are complex and that a number of specific factors are involved in these events.

One of the *Drosophila* segment polarity genes, porcupine (porc) encodes a multipass transmembrane ER protein, which is required for the normal distribution of Wg in embryos (Kadowaki T, et al, 1996). In porc mutant embryos, Wg is sequestered in its synthesizing cells and not distributed among the surrounding cells. Wg signaling components are well conserved in multicellular organisms, and porc homologs are also present in other species. *C. elegans* porc homolog mom-1 is necessary in Mom-2 producing cells as Porc is required in Wg-synthesizing cells (Thorpe C J, et al, 1997). Vertebrate (mouse and *Xenopus*) homologues of porc have been shown to modify the N-glycosylation of Wg and mouse Wnt proteins in cultured cells (Tanaka K, et al, 2000).

Recently, the human homologue of the *Drosophila* gene Porcupine (Porc) has also been cloned (Caricasole A, et al, 2002). The human Porcupine locus (PPN/MG61) spans 15 exons over approximately 12 kb of genomic sequence on Xp 11.23. Like its mouse and *Xenopus* homologues, PPN/MG61 is expressed in a tissue-specific fashion. Evidence also indicates that human PPN/MG61 can influence the activity of a human Wnt7A expression construct in a T-cell factor-responsive reporter assay. These results demonstrate that the porc gene family encodes the evolutionary conserved ER membrane proteins involved in the processing of the Wnt family.

Based on the amino acid sequence conservation between Porc and other membrane-bound acyltransferase superfamily, Porc is likely to function as the acyltransferase of Wnt (Hofmann K, 2000). Porc acylates Wnt proteins and anchors them at the ER membrane to stimulate their post-translational N-glycosylation, which is necessary for secretion. In the absence of porc, Wnt proteins are not secreted from the synthesizing cells, and therefore Wnt signaling is not activated in the surrounding cells.

All biochemically characterized members of the membrane-bound acyltransferase superfamily encode enzymes that transfer organic acids, typically fatty acids, onto hydroxyl groups of membrane-embedded targets. Examples include ACAT (cholesterol acyltransferase; transferring fatty acids to cholesterol), Are ½ (transferring fatty acids to yeast sterols), DGAT (diacylglycerol O-acyltranserase; transferring fatty acids to diacylglycerol), wax synthase (transferring fatty acids to long-chain alcohols), DltB (involved in the incorporation of alanine into lipoteichoic acids) and AlgI (involved in alginate O-acetylation) (Hofmann K, 2000). The presumed enzymatic role of the protein family is corroborated by the conservation of polar residues within and adjacent to the membrane. Most notably, a histidine positioned within a long hydrophobic region is invariant, making it a likely active-site residue.

Other members of the superfamily have been characterized only genetically. These include the *Drosophila* gene porcupine along with its nematode homolog mom-1 Porcupine is essential for Wingless signaling and affects Wingless processing and secretion (Kadowaki T, et al, 1996). Mom-1 was identified in a genetic screen for endoderm differentiation mutants, along with mom-2 (a wingless homolog) and mom-5 (a frizzled homolog) (Thorpe C J, et al, 1997). A role for the Porcupine-like proteins in Wingless signaling is well established. Based on the homology their mode of action as an acyltransferases appears plausible. However, the nature of the substrate is still an open question. These observations are not the only links between acylation and Wnt signaling. Members of the Dickkopf (DKK) family of Wnt inhibitors were found to be related to collapses (Aravind L and Koonin E V, 1998). Therefore, there is a hint that deacylation mediated by Dickkopf (DKK) proteins might be antagonistic to acylation mediated by Porcupine (Porc; PPN/MG61).

The Wnt/Frizzled receptor pathway involves important regulatory genes that carry polymorphisms associated with primary carcinomas. In the course of downstream signaling cytosolic β-catenin accumulates, translocates into the nucleus, and then enhances gene expression by complexing with other transcription factors. In the absence of Wnt signals, free cytosolic β-catenin is incorporated into a complex consisting of Axin, the adenomatous polyposis coli (APC) gene product, and glycogen synthase kinase (GSK)-3β. Conjunctional phosphorylation of Axin, APC, and β-catenin by GSK-3β designates β-catenin for the ubiquitin pathway and degradation by proteasomes.

It is known that Wnt/β-catenin signaling promotes cell survival in various cell types. Wnt signaling pathway is also thought to be associated with tumor development and/or progression. Aberrant activation of the Wnt signaling pathway is associated with a variety of human cancers. For example, mutations in the gene APC are an initiating event for both sporadic and hereditary colorectal tumorigenesis. APC mutants are relevant in tumorigenesis, since the aberrant protein is an integral part of the Wnt-signaling cascade. The protein product contains several functional domains acting as binding and degradation sites for β-catenin. Mutations that occur in the amino-terminal segment of β-catenin are usually involved in phosphorylation-dependent, ubiquitin-mediated degradation and, thus, stabilize β-catenin. When stabilized cytoplasmic-catenin accumulates, it translocates to the nucleus interacting with the Tcf/Lef high-mobility group of transcription factors that modulate expression of oncogenes such as c-Myc. Evidence has also shown that Wnt proteins are over-expressed and aberrantly activated in a variety of cancers. However, the role of the Wnt signaling pathway in oncogenesis remains unclear.

The method of the present invention demonstrates that human homologue of *Drosophila* Porcupine gene, PPN/MG61, is expressed abundantly in a variety of human cancer cell lines, including lung cancer, breast cancer, colorectal cancer, mesothelioma, head and neck cancer and melanoma. In contrast, PPN/MG61 expression was not observed in cultured normal cells. The present method further demonstrates that the PPN/MG61 are over-expressed in primary lung cancer and mesothelioma tissue samples, which was not expressed in their matched normal tissue samples (from same patients). In addition, PPN/MG61 expression was detected in serum from patients of a variety of cancers, including lung cancer and thyroid cancer, etc, but not in normal serum samples.

The method of the present invention also demonstrates the overexpression of human PPN/MG61 is necessary for survival of cancer cells. Knocking-down PPN/MG61 mRNA and/or inhibiting the acyltransferase activity of PPN/MG61 induce apoptosis in many types of cancers, especially lung cancer and mesothelioma. These data suggest that lipid modification of the Wnt signaling molecules by PPN/MG61 is important for function of the pathway in tumorigenesis, and that PPN/MG61 could be a provocative therapeutic target. Thus, detection of PPN/MG61 expression and inhibition of PPN/MG61 enzyme activity may have widespread implications for molecular diagnosis, early detection and treatment of human cancers.

SUMMARY OF THE INVENTION

This invention provides diagnostic methods of detecting the PPN/MG61 expression and/or enzyme activity in human cell, tissue and body fluid including serum and sputum, and inhibiting the growth of a cancer cell that overexpresses PPN/MG61 by inhibiting the acyltransferase activity.

In one embodiment, the present invention provides a method for measuring the gene transcript (e.g. mRNA) of PPN/MG61 by using reverse transcription PCR (RT-PCR), or by using amplification (e.g. PCR) based methods for directly assessing copy number of DNA.

In a second embodiment, the present invention provides a method for measuring the quantity of PPN/MG61 proteins, or cells expressing them, using any of a number of well recognized immunological binding assays, including ELISA (Enzyme-Linked Immunosorbent Assay) using monospecific antibody that binds to PPN/MG61.

Translated protein level of PPN/MG61 can also be detected by using any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like. The isolated proteins can also be sequence according to standard techniques to identify polymorphisms.

In a third embodiment, the present invention provides a method for measuring and/or quantifying the enzyme (O-acyltransferase) activity of PPN/MG61 by using conversion of its substrates.

The measured difference in the expression levels and/or enzyme activity of PPN/MG61 by the first and second cells is used to detect or diagnose a cancer, diagnose the metastatic potential of a cancer, monitor the prognosis and progression of a cancer, or monitor the therapeutic efficacy of a treatment of a cancer. The cancer includes, but is not limited to, lung carcinoma, breast carcinoma, colorectal carcinoma, carcinoid, gastric carcinoma, glioma, hepatocellular carcinoma, leiomyosarcoma, liver carcinoma, kidney cancer, bladder cancer, uterus cancer, head and neck cancer, vulval or testical cancer, brain tumor, cervical cancer, esophageal cancer, lymphoma, melanoma, mesothelioma, myeloma, ovarian carcinoma, pancreas carcinoma, prostate carcinoma, thyroid carcinoma, renal cell carcinoma, retinoblastoma, rhabdomyosarcoma, sarcoma, undifferentiated carcinoma, and leukemia.

In a fourth embodiment, the present invention provides a method for making Kits for detecting the expression levels and/or enzyme activity of PPN/MG61 disclosed in this invention, which can be used to detect or diagnose a cancer, diagnose the metastatic potential of a cancer, monitor the prognosis and progression of a cancer, or monitor the therapeutic efficacy of a treatment of a cancer.

In another embodiment, the present method provides a method for in vitro and in vivo imaging of a tissue.

In yet another embodiment, the present invention provides a method and/or the Kits disclosed in this invention for screening a therapeutically effective compound that inhibits PPN/MG61.

The PPN/MG61 specific compounds encompassed by the invention include, but are not limited to, a small molecule compound that binds to PPN/MG61, mimic its substrates and inhibit its enzyme activity, a peptide or a monospecific antibody that binds to PPN/MG61 protein or a nucleic acid probe/primer that will hybridize with PPN/MG61 mRNA/cDNA.

A still further embodiment of the present method includes a method for treating a PPN/MG61 mediated cancer in a subject in need thereof comprising administering a therapeutically effective amount of a pharmaceutical formulation of a PPN/MG61 inhibitor compound to the subject; wherein, optionally, the PPN/MG61 inhibitor compound is cytotoxic. Preferred PPN/MG61 inhibitor compounds include, but are not limited to, a PPN/MG61 specific compound. In a preferred embodiment of this aspect of the invention, the pharmaceutical formulation is coated onto a balloon catheter or stent and released in a time-dependent manner. It further comprises administering to a cancer patient alone and/or with a second therapeutic agent (e.g. chemotherapeutic agent and/or radiation therapy).

BRIEF DESCRIPTION OF DRAWINGS

FIG. 13. Multiple alignment of a conserved region in the membrane-bound O-acyltransferase family. Only selected proteins are shown. Species and enzyme names are abbreviated: AT, *Arabidopsis thaliana*; BS, *Bacillus subtilis*; CE, *Caenorhabditis elegans*; DM, *Drosophila melanogaster*; HS, *Homo sapiens*; MM, *Mus musculus*; PA, *Pseudomonas aeruginosa*; SA, *Staphylococcus aureus*; SC, *Saccharomyces cerevisiae*; SI, *Simmondsia chinensis*; TP, *Treponema pallidum*; ACAT, cholesterol acyltransferase; DGAT, diacylglycerol O-acyltransferase; WaxSyn, wax synthase.

DETAILED DESCRIPTION OF PARTICULAR EMBODIMENTS

Figure 1:
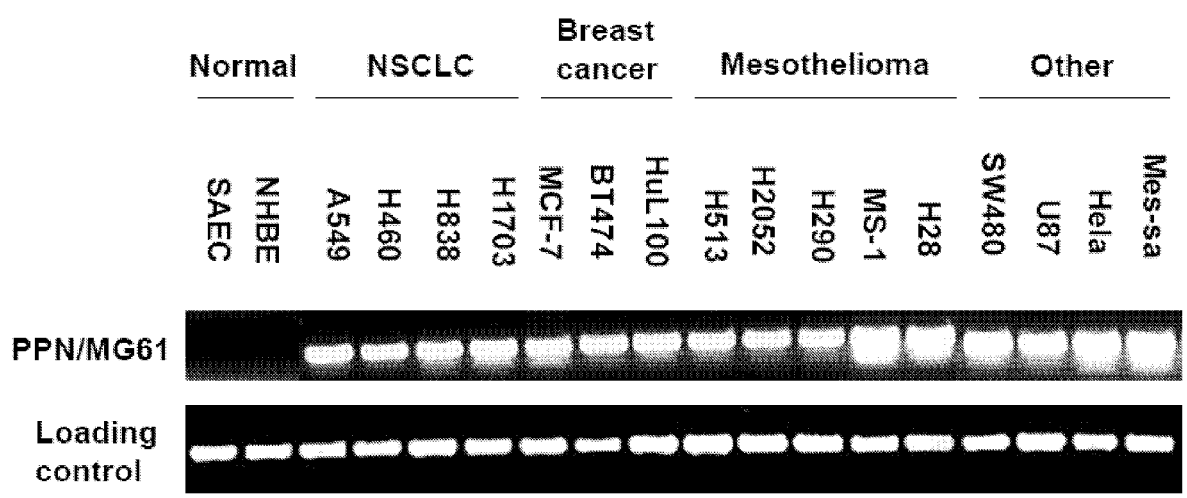
FIG. 1. PPN/MG61 expression in human normal and cancer cell lines. RT-PCR analysis of PPN/MG61 expression in various cancer cell lines, The cell lines used include non-small cell lung cancer (NSCLC) cell lines (A549, H460, H838 and H1703), breast cancer cell lines (MCF-7, BT474 and HuL100), malignant plural mesothelioma cell lines (H513, H2052, H290, MS-1 and H28), colon cancer cell line (SW480), head and neck cancer cell line (U87), Hela cell line, sarcoma cell line (Mes-SA) and normal cells (small airway epithelial cells (SAEC), bronchial epithelial cells (NHBE)). Total RNA from each cell type was prepared.

Definitions:

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences (See J. Mol. Biol. 48: 443-453 (1970)). Of interest is the BestFit program using the local homology algorithm of Smith Waterman (Advances in Applied Mathematics 2: 482-489 (1981)) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA. The percentage of the alignment region length is calculated by counting the number of residues of the individual sequence found in the region of strongest alignment. This number is divided by the total residue length of the target or query polynucleotide sequence to find a percentage. Percent sequence identity is calculated by counting the number of residue matches between the target and query polynucleotide sequence and dividing total number of matches by the number of residues of the target or query sequence found in the region of strongest alignment.

The phrase "PPN/MG61 specific compound" refers to, for example, synthetic or natural amino acid polypeptides, proteins, small synthetic organic molecules, or deoxy- or ribonucleic acid sequences that bind to PPN/MG61 with about 20-fold or greater affinity compared to other proteins or nucleic acids. For example, but not by way of limitation, polyclonal or monoclonal (including classical or phage display) antibodies raised against the PPN/MG61 protein or a peptide fragment thereof or nucleic acid probes that hybridize with PPN/MG61 mRNA.

As used herein, a "therapeutically effective amount" of the instant pharmaceutical composition, or compound therein, means an amount that inhibits the function of the PPN/MG61 activity. The instant pharmaceutical composition will generally contain a per dosage unit (e.g., tablet, capsule, powder, injection, teaspoonful and the like) from about 0.001 to about 100 mg/kg. In one embodiment, the instant pharmaceutical composition contains a per dosage unit of from about 0.01 to about 50 mg/kg of compound, and preferably from about 0.05 to about 20 mg/kg. Methods are known in the art for determining therapeutically effective doses for the instant pharmaceutical composition. The effective dose for administering the pharmaceutical composition to a human, for example, can be determined mathematically from the results of animal studies. Furthermore, compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The terms "individual," "subject," "host," and "patient," used interchangeably herein, refer to a mammal, including, but not limited to, murines, simians, humans, felines, canines, equines, bovines, mammalian farm animals, mammalian sport animals, and mammalian pets.

The present invention provides evidence, for the first time, that the human PPN/MG61, likely functioning as an acyltransferase, is upregulated in certain tissue disease states. In particular, PPN/MG61 is expressed abundantly in a variety of human cancers, including lung cancer, breast cancer, colorectal cancer, mesothelioma, head and neck cancer and melanoma. In contrast, PPN/MG61 expression was not observed in cultured normal cells.

The present invention also provides evidence, for the first time, that the over-expression of human PPN/MG61 is necessary for survival of cancer cells. Knocking-down PPN/MG61 mRNA and/or inhibiting the acyltransferase activity of PPN/MG61 induce apoptosis in many types of cancers, especially lung cancer.

Therefore, detecting the presence of and measuring the amount of PPN/MG61 in a cell or detecting the presence of PPN/MG61 in vivo provides a method for diagnosing or monitoring disease states, including, but not by way of limitation, cancer and tumor metastasis. Accordingly, inhibiting the upregulation or unregulated overexpression of PPN/MG61 provides a method for treating a disease state, particularly cancer mediated by the expression of PPN/MG61.

The human cells in the present application are selected from the group consisting of adrenal cells, brain cells, breast cells, colon cells, epithelial cells, endothelial cells, heart cells, immunological cells, kidney cells, liver cells, lung cells, ovary cells, pancreas cells, prostate cells, skin cells, spleen cells, stomach cells, testis cells, thyroid cells, uterus cells and vascular cells, wherein the epithelial cells are selected from the group consisting of endothelial cells, non-glial neuronal cells, colon cells, breast cells, the proximal tubules of the kidney, smooth muscle of the prostate, smooth muscle of the uterus and smooth muscle of the testis, and the immunological cells are selected from the group consisting of polymorphonuclear leukocytes, monocytes, macrophages, epithelioid cells, giant cells, microglia, Kupffer cells and alveolar macrophages.

The present invention further provides compositions, including pharmaceutical compositions, comprising the polypeptides, polynucleotides, antibodies, recombinant vectors, and host cells of the invention. These compositions may include a buffer, which is selected according to the desired use of the polypeptide, antibody, polynucleotide, recombinant vector, or host cell, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein.

The invention provides antibodies that are specific for PPN/MG61. Suitable antibodies are obtained by immunizing a host animal with peptides comprising all or a portion of the target protein. Suitable host animals include mouse, rat sheep, goat, hamster, rabbit, etc. The origin of the protein immunogen may be mouse, human, rat, monkey etc. The host animal will generally be a different species than the immunogen, e.g. human protein used to immunize mice, etc.

The immunogen may comprise the complete protein, or fragments and derivatives thereof. Preferred immunogens comprise all or a part of one of the subject proteins, where these residues contain the post-translation modifications, such as glycosylation, found on the native target protein. Immunogens comprising the extracellular domain are produced in a variety of ways known in the art, e.g. expression of cloned genes using conventional recombinant methods, isolation from tumor cell culture supernatants, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ELISA, ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, protein G sepharose, etc.

The antibody may be produced as a single chain, instead of the normal multimeric structure. Single chain antibodies are described in Jost et al. (1994) J. B. C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) P.N.A.S. 84:3439 and (1987) J. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies that are identical to human antibodies may be employed. By xenogenic human antibodies is meant antibodies that are the same has human antibodies, i.e. they are fully human antibodies, with exception that they are produced using a non-human host which has been genetically engineered to express human antibodies. See e.g. WO 98150433; WO 98,24893 and WO 99/53049, the disclosures of which are herein incorporated by reference.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, Rous sarcoma virus LTR and moloney murine leukemia virus LTR; native Ig promoters, etc.

The subject polypeptide and nucleic acid compositions find use in a variety of different applications. Applications of interest include: research, diagnostic, and therapeutic agent screening/discovery/preparation applications, as well as therapeutic compositions. Applications of interest also include: the identification of homologs of PPN/MG61; as a source of novel promoter elements; the identification of expression regulatory factors; as probes and primers in hybridization applications, e.g. polymerase chain reaction (PCR); the identification of expression patterns in biological specimens; the preparation of cell or animal models for function of PPN/MG61; the preparation of in vitro models for function of PPN/MG61; etc.

Homologs are identified by any of a number of methods. A fragment of the provided cDNA may be used as a hybridization probe against a cDNA library from the target organism of interest. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided nucleic acid sequences, e.g. Seq ID No: 2, genetically altered versions of the gene, etc., bind to the provided sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where the subject genes are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease, particularly cancer.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc.

The regulatory sequences may be used to identify cis acting sequences required for transcriptional or translational regulation of expression, especially in different tissues or stages of development, and to identify cis acting sequences and transacting factors that regulate or mediate expression. Such transcription or translational control regions may be operably linked to a gene in order to promote expression of wild type or proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. It is preferable to choose a pair of primers that will generate an amplification product of at least about 50 nt, preferably at least about 100-300 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of gene expression in the sample.

The sequence of a gene according to the subject invention, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

The subject nucleic acids can be used to generate transgenic, non-human animals or site-specific gene modifications in cell lines. Thus, in some embodiments, the invention provides a non-human transgenic animal comprising, as a transgene integrated into the genome of the animal, a nucleic acid molecule comprising a sequence PPN/MG61 in operable linkage with a promoter, such that PPN/MG61-encoding nucleic acid molecule is expressed in a cell of the animal. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

The modified cells or animals are useful in the study of gene function and regulation. For example, a series of small deletions and/or substitutions may be made in the host's native gene to determine the role of different exons in oncogenesis, signal transduction, etc. Of interest is the use of genes to construct transgenic animal models for cancer, where expression of the subject protein is specifically reduced or absent. Specific constructs of interest include antisense constructs, small interfering RNA (siRNA), short-hairpin RNA (shRNA), which block PPN/MG61 expression; expression of dominant negative mutations; and over-expression of genes. Where a sequence is introduced, the introduced sequence may be either a complete or partial sequence of a gene native to the host, or may be a complete or partial sequence that is exogenous to the host animal, e.g., a human sequence of the subject invention. A detectable marker, such as lac Z may be introduced into the locus, where upregulation of expression will result in an easily detected change in phenotype.

One may also provide for expression of the gene, e.g. the PPN/MG61 gene, or variants thereof in cells or tissues where it is not normally expressed, at levels not normally present in such cells or tissues, or at abnormal times of development. One may also generate host cells (including host cells in transgenic animals) that comprise a heterologous nucleic acid molecule that encodes a polypeptide which functions to modulate expression of an endogenous PPN/MG61 promoter or other transcriptional regulatory region.

DNA constructs for homologous recombination will comprise at least a portion of the human gene or of a gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on PPN/MG61 activity.

The present invention also provides methods of diagnosing disease states, particularly cancer, based on observed levels and/or activity of PPN/MG61 and/or the level of PPN/MG61 polynucleotide in a biological sample of interest. Samples, as used herein, include biological fluids such as blood, cerebrospinal fluid, tears, saliva, lymph, dialysis fluid, breast ductal lavage fluid, semen and the like; cells; organ or tissue culture derived fluids; tumor biopsy samples; stool samples; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Detection methods of the invention may be qualitative or quantitative. Thus, as used herein, the terms "detection," "determination," and the like, refer to both qualitative and quantitative determinations, and include "measuring."

Detection methods of the present invention include methods for detecting PPN/MG61 polypeptide in a biological sample, methods for detecting PPN/MG61 mRNA in a biological sample, and methods for detecting PPN/MG61 enzymatic activity in a biological sample.

In some embodiments, the detection methods provide for detection of cancerous cells in a biological sample (e.g., blood, serum). As described in the Examples, human PPN/MG61 mRNA levels are elevated in particular cancers, e.g., lung cancer, breast cancer, colorectal cancer and mesothelioma. Thus, detection of an mRNA encoding PPN/MG61 at an elevated level compared to normal (non-cancerous) tissue, provides for detection of cancerous tissue in a biological sample.

The detection methods can be provided as part of a Kit. Thus, the present invention further provides Kits for detecting the presence and/or a level of PPN/MG61 polypeptide or PPN/MG61 polynucleotide in a biological sample. Procedures using these Kits can be performed by clinical laboratories, experimental laboratories, medical practitioners, or private individuals. The Kits of the present invention for detecting a PPN/MG61 polypeptide comprise a moiety that specifically binds PPN/MG61, including, but not limited to, a PPN/MG61-specific compound or antibody. The Kits of the present invention for detecting a PPN/MG61 polynucleotide comprise a moiety that specifically hybridizes to a PPN/MG61 polynucleotide.

In some embodiments, a Kit of the invention for detecting a PPN/MG61 polynucleotide, such as an mRNA encoding PPN/MG61, comprises a pair of nucleic acids that function as "forward" and "reverse" primers that specifically amplify a cDNA copy of PPN/MG61-encoding mRNA. The "forward" and "reverse" primers are provided in the kit as a pair of isolated nucleic acid molecules, each from about 10 to 200 nucleotides in length, the first nucleic acid molecule of the pair comprising a sequence of at least 10 contiguous nucleotides having 100% sequence identity to the nucleic acid sequence set forth in SEQ ID NO: 02, and the second nucleic acid molecule of the pair comprising a sequence of at least 10 contiguous nucleotides having 100% sequence identity to the reverse complement of the nucleic acid sequence set forth in SEQ ID NO: 02, wherein the sequence of the second nucleic acid molecule is located 3' of the nucleic acid sequence of the first nucleic acid molecule in SEQ ID NO: 02. The primer nucleic acids are prepared using any known method, e.g., automated synthesis, and the like. SEQ ID NO: 3, 4, 5, 6, 7, 8, 9, 10, 11 and 12 are some examples for the "forward" and "reverse" primers.

The invention provides a Kit comprising a pair of nucleic acids as described above. The nucleic acids are present in a suitable storage medium, e.g., buffered solution, typically in a suitable container. The kit includes the pair of nucleic acids, and may further include a buffer; reagents for polymerase chain reaction (PCR) (e.g., deoxynucleotide triphosphates (dATP, dTTP, dCTP, and dGTP), a thermostable DNA polymerase, a reverse transcriptase, a buffer suitable for PCR, a solution containing $Mg^{2+}$ ions (e.g., $MgCl_2$), and other components well known to those skilled in the art for carrying out a PCR, or reverse transcriptional-PCR (RT-PCR), or Real-time RT-PCR. The kit may further include instructions for use of the kit, which instructions may be provided in a variety of forms, e.g., as printed information, on a compact disc, and the like. The kit may further include reagents necessary for extraction of DNA from a biological sample (e.g., blood, serum sample, biopsy sample, and the like) from an individual, and reagents for generating a cDNA copy of a mRNA. The kits are useful in diagnostic applications, as described in more detail below. The pair of isolated nucleic acid molecules serves as primers in an amplification reaction (e.g., a PCR, RT-PCR, or Real-time RT-PCR).

In some embodiments, the first and/or the second nucleic acid molecules comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{31}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The kit may optionally provide additional components that are useful in the procedure, including, but not limited to, buffers, developing reagents, labels, reacting surfaces, means for detections, control samples, standards, instructions, and interpretive information.

Where the kit provides for detection of a PPN/MG61 polypeptide, the kit includes one or more antibodies specific for the subject PPN/MG61. In some embodiments, the antibody specific for the subject PPN/MG61 is detectably labeled. In other embodiments, the antibody specific for the subject PPN/MG61 is not labeled; instead, a second, detectably-labeled antibody is provided that binds to the antibody specific for a subject PPN/MG61 (the "first" antibody). The kit may further include blocking reagents, buffers, and reagents for developing and/or detecting the detectable marker. The kit may further include instructions for use, controls, and interpretive information.

Where the kit provides for detecting enzymatic activity of PPN/MG61, the kit includes a substrate that provides for a detectable product when acted upon by PPN/MG61. Suitable substrates are discussed in detail below. The kit may further include reagents necessary for detectable marker development and detection. The kit may further include instructions for use, controls, and interpretive information.

The present invention further provides methods for detecting the presence and/or measuring a level of a PPN/MG61 polypeptide in a biological sample, using a PPN/MG61-specific antibody. The methods generally comprise: a) contacting the sample with an antibody specific for a PPN/MG61 polypeptide; and b) detecting binding between the antibody and molecules of the sample.

Detection of specific binding of the PPN/MG61-specific antibody, when compared to a suitable control, is an indication that PPN/MG61 polypeptides are present in the sample. Suitable controls include a sample known not to contain a PPN/MG61 polypeptide; and a sample contacted with an antibody not specific for PPN/MG61, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the PPN/MG61-specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthamide series, attached to the antibody through metal chelating groups such as EDTA; chemiluminescent compounds, e.g., luminol, isoluminol, acridinium salts, and the like; bioluminescent compounds, e.g., luciferin, green fluorescent protein, and the like.

The antibody may be attached (coupled) to an insoluble support, such as a polystyrene plate or a bead. Indirect labels include second antibodies specific for PPN/MG61-specific antibodies, wherein the second antibody is labeled as described above; and members of specific binding pairs, e.g., biotin-avidin, and the like. The biological sample may be brought into contact with an immobilized on a solid support or carrier, such as nitrocellulose, that is capable of immobilizing cells, cell particles, or soluble proteins. The support may then be washed with suitable buffers, followed by contacting with a detectably-labeled PPN/MG61-specific antibody. Detection methods are known in the art and will be chosen as appropriate to the signal emitted by the detectable label. Detection is generally accomplished in comparison to suitable controls, and to appropriate standards.

The present invention further provides methods for detecting the presence and/or levels of enzymatic activity of PPN/MG61 in a biological sample. The methods generally involve: a) contacting the sample with a substrate that yields a detectable product upon being acted upon by PPN/MG61; and b) detecting a product of the enzymatic reaction.

Any acylated compound that, upon cleavage of the acyl-group by the acyltransferase activity of PPN/MG61, results in a change in absorption, fluorescence or other physical property amenable to detection, is suitable for use in a subject assay.

The present invention further provides methods for detecting the presence of PPN/MG61 mRNA in a biological sample. The methods can be used, for example, to assess whether a test compound affects PPN/MG61 gene expression, directly or indirectly. The methods generally comprise: a) contacting the sample with a PPN/MG61 polynucleotide of the invention under conditions that allow hybridization; and b) detecting hybridization, if any.

Detection of hybridization, when compared to a suitable control, is an indication of the presence in the sample of a PPN/MG61 polynucleotide. Appropriate controls include, for example, a sample which is known not to contain PPN/MG61 mRNA, and use of a labelled polynucleotide of the same "sense" as a PPN/MG61 mRNA. Conditions that allow hybridization are known in the art, and have been described in more detail above. Detection can be accomplished by any known method, including, but not limited to, in situ hybridization, PCR, RT-PCR, real-time RT-PCR and "Northern" or RNA blotting, or combinations of such techniques, using a suitably labelled PPN/MG61 polynucleotide. A variety of labels and labelling methods for polynucleotides are known in the art and can be used in the assay methods of the invention. Specific hybridization can be determined by comparison to appropriate controls.

In some embodiments, the methods involve generating a cDNA copy of an mRNA molecule in a biological sample, and amplifying the cDNA using a pair of isolated nucleic acid molecules that serve as forward and reverse primers in an amplification reaction (e.g., a PCR). Each of the nucleic acid molecules in the pair of nuclei acid molecules is from about 10 to 200 nucleotides in length, the first nucleic acid molecule of the pair comprising a sequence of at least 10 contiguous nucleotides having 100% sequence identity to the nucleic acid sequence set forth in SEQ ID NO: 02, and the second nucleic acid molecule of the pair comprising a sequence of at least 10 contiguous nucleotides having 100% sequence identity to the reverse complement of the nucleic acid sequence set forth in SEQ ID NO: 02, wherein the sequence of the second nucleic acid molecule is located 3' of the nucleic acid sequence of the first nucleic acid molecule in SEQ ID NO: 02. The primer nucleic acids are prepared using any known method, e.g., automated synthesis, and the like. The primer pairs are chosen such that they specifically amplify a cDNA copy of an mRNA encoding PPN/MG61. SEQ ID NO: 3, 4, 5, 6, 7, 8, 9, 10, 11 and 12 are some examples for the "forward" and "reverse" primers.

Methods using PCR amplification can be performed on the DNA from a single cell, although it is convenient to use at least about $10^5$ cells. The use of the polymerase chain reaction is described in Saiki et al. (1985) *Science* 239:487, and a review of current techniques may be found in Sambrook, et al. *Molecular Cloning: A Laboratory Manual* CSH Press 1989, pp. 14.2-14.33. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, etc. having a high affinity binding partner, e.g. avidin, specific antibodies, etc., where the binding partner is conjugated to a detectable label. The label may be conjugated to one or both of the primers. Alternatively, the pool of nucleotides used in the PCR is labeled, so as to incorporate the label into the amplification product.

A number of methods are available for determining the expression level of a gene or protein in a particular sample. Diagnosis may be performed by a number of methods to determine the absence or presence or altered amounts of normal or abnormal PPN/MG61 in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of the subject PPN/MG61 genes. Biochemical studies may be performed to determine whether a sequence polymorphism in a coding region or control regions is associated with disease. Disease associated polymorphisms may include deletion or truncation of the gene, mutations that alter expression level, that affect the activity of the protein, etc.

Changes in the promoter or enhancer sequence that may affect expression levels of the subject genes can be compared to expression levels of the normal allele by various methods known in the art. Methods for determining promoter or enhancer strength include quantitation of the expressed natural protein; insertion of the variant control element into a vector with a reporter gene such as chloramphenicol acetyltransferase, luciferase, β-galactosidase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express the gene may be used as a source of mRNA, which may be assayed directly or reverse transcribed into cDNA for analysis. The nucleic acid may be amplified by conventional techniques, such as PCR, to provide sufficient amounts for analysis. The use of the PCR is described in Saiki, et al. (1985), *Science* 239:487, and a review of techniques may be found in Sambrook, et al. *Molecular Cloning: A Laboratory Manual*, CSH Press 1989, pp. 14.2-14.33. Alternatively, various methods are known in the art that utilize oligonucleotide ligation as a means of detecting polymorphisms, for example, Riley et al. (1990), *Nucl. Acids Res.* 18:2887-2890; and Delahunty et al. (1996), *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, eg. $^{32}$P, $^{35}$S, $^{3}$H; etc. The label may be a two stage system, where the amplified DNA is conjugated to biotin, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type sequence. Hybridization with the variant sequence may also be used to determine its presence, by Southern blots, dot blots, etc. The hybridization pattern of a control and variant sequence to an array of oligonucleotide probes immobilized on a solid support, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in the gene may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity of the encoded protein may be determined by comparison with the wild-type protein.

Diagnostic methods of the subject invention in which the level of expression is of interest will typically involve comparison of the nucleic acid abundance of a sample of interest with that of a control value to determine any relative differences, where the difference may be measured qualitatively and/or quantitatively, which differences are then related to the presence or absence of an abnormal expression pattern. A variety of different methods for determining the nucleic acid abundance in a sample are known to those of skill in the art, where particular methods of interest include those described in: Pietu et al., Genome Res. (June 1996) 8: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; and Chalifour et al., Anal. Biochem (Feb. 1, 1994) 216: 299-304.

The present invention provides screening methods for identifying agents which modulate PPN/MG61 enzyme activity, methods for identifying agents which modulate a level of a subject PPN/MG61 polypeptide in a cell; and methods for identifying agents which modulate a level of a subject PPN/MG61 mRNA in a cell; and methods for identifying agents that modulate release of a subject PPN/MG61 from a eukaryotic cell. In some embodiments, the assay is a cell-free assay. In other embodiments, the assay is a cell-based assay.

As used herein, the term "modulate" encompasses "increase" and "decrease." In some embodiments, of particular interest are agents which inhibit PPN/MG61 activity, and/or which reduce a level of a subject PPN/MG61 polypeptide in a cell, and/or which reduce a level of a subject PPN/MG61 mRNA in a cell and/or which reduce release of PPN/MG61 from a eukaryotic cell. Such agents are of interest as candidates for treating cancers. In other embodiments, agents of interest are those that increase PPN/MG61 activity; such agents are of interest as candidates for treating disorders amenable to treatment by increasing angiogenesis, e.g., ischemic conditions.

The terms "candidate agent," "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

The present invention provides methods of identifying agents that modulate an enzymatic activity of a PPN/MG61 polypeptide of the invention. The term "modulate" encompasses an increase or a decrease in the measured PPN/MG61 activity when compared to a suitable control.

The method mentioned above generally comprises: a) contacting a test agent with a sample containing a PPN/MG61 polypeptide; and b) assaying the acyltransferase activity of the PPN/MG61 polypeptide in the presence of the substance. An increase or a decrease in PPN/MG61 activity in comparison to PPN/MG61 activity in a suitable control (e.g., a sample comprising a PPN/MG61 polypeptide in the absence of the substance being tested) is an indication that the substance modulates an enzymatic activity of PPN/MG61.

An "agent that modulates the acyltransferase activity of a PPN/MG61 polypeptide", as used herein, describes any molecule, e.g. synthetic or natural organic or inorganic compound, protein or pharmaceutical, with the capability of altering modulates the acyltransferase activity of a PPN/MG61 polypeptide, as described herein. Generally a plurality of assay mixtures is run in parallel with different agent concentrations to obtain a differential response to the various concentrations. Typically, one of the concentrations serves as a negative control, i.e. at zero concentration or below the level of detection. Acyltransferase activity can be measured using any kinase assay known in the art.

Any acylated compound that, upon cleavage of the acyl-group by the acyltransferase activity, results in a change in absorption, fluorescence or other physical property amenable to detection, is suitable for use in a subject assay.

In certain embodiments, a substrate comprising a $^{35}$S label is used. Release of $^{35}$S is measured using any appropriate assay, e.g., scintillation counting, and the like.

In other embodiments, the substrate comprises an acylated moiety that provides a detectable signal once the acyl-group is released by action of the acyltransferase. Acyltransferase activity may be detected by measuring fluorescence. This assay may be particularly suited to a high-through-put format.

An agent which modulates the acyltransferase activity of a subject PPN/MG61 polypeptide increases or decreases the activity at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

Agents that increase or decrease the acyltransferase activity of a subject PPN/MG61 polypeptide to the desired extent may be selected for further study, and assessed for cellular availability, cytotoxicity, biocompatibility, etc.

Of particular interest in some embodiments are agents that decrease the acyltransferase activity of a subject PPN/MG61 polypeptide. Maximal inhibition of acyltransferase activity is not always necessary, or even desired, in every instance to achieve a therapeutic effect. Agents that decrease the acyltransferase activity of a subject PPN/MG61 polypeptide may find use in reducing Wnt signaling and/or angiogenesis stimulated by a tumor cell and thus may be useful in treating cancers.

Of particular interest in some embodiments are agents that increase the acyltransferase activity of a subject PPN/MG61 polypeptide. Agents that increase the acyltransferase activity of a subject PPN/MG61 polypeptide may find use in increasing angiogenesis and thus may be useful in treating ischemic conditions.

Cell-based methods include methods of detecting an agent that modulates a level of PPN/MG61 mRNA and/or PPN/MG61 polypeptides, and methods for detecting an agent that modulates release of PPN/MG61 from a eukaryotic cell.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

The cells used in the assay are usually mammalian cells, including, but not limited to, human cells. The cells may be primary cell cultures or may be immortalized cell lines.

A wide variety of cell-based assays may be used for identifying agents which modulate levels of PPN/MG61 mRNA and for identifying agents that modulate release of PPN/MG61 from a eukaryotic cell, using, for example, a mammalian cell transformed with a construct comprising a PPN/MG61-encoding cDNA such that the cDNA is overexpressed, or, alternatively, a construct comprising a PPN/MG61 promoter linked to a reporter gene.

Accordingly, the present invention provides a method for identifying an agent, particularly a biologically active agent, that modulates a level of PPN/MG61 expression in a cell, the method comprising: combining a candidate agent to be tested with a cell comprising a nucleic acid which encodes a PPN/MG61 polypeptide; and determining the effect of said agent on PPN/MG61 expression. "Modulation" of PPN/MG61 expression levels includes increasing the level and decreasing the level of PPN/MG61 mRNA and/or PPN/MG61 polypeptide encoded by the PPN/MG61 polynucleotide when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of PPN/MG61 mRNA and/or polypeptide following contacting the cell with a candidate agent being tested, compared to a control to which no agent is added, is an indication that the agent modulates PPN/MG61 expression.

PPN/MG61 mRNA and/or polypeptide whose levels are being measured can be encoded by an endogenous PPN/MG61 polynucleotide, or the PPN/MG61 polynucleotide can be one that is comprised within a recombinant vector and introduced into the cell, i.e., the PPN/MG61 mRNA and/or polypeptide can be encoded by an exogenous PPN/MG61 polynucleotide. For example, a recombinant vector may comprise an isolated PPN/MG61 transcriptional regulatory sequence, such as a promoter sequence, operably linked to a reporter gene (e.g., β-galactosidase, CAT, luciferase, or other gene that can be easily assayed for expression). In these embodiments, the method for identifying an agent that modulates a level of PPN/MG61 expression in a cell, comprises: combining a candidate agent to be tested with a cell comprising a nucleic acid which comprises a PPN/MG61 gene transcriptional regulatory element operably linked to a reporter gene; and determining the effect of said agent on reporter gene expression. A recombinant vector may comprise an isolated PPN/MG61 transcriptional regulatory sequence, such as a promoter sequence, operably linked to sequences coding for a PPN/MG61 polypeptide; or the transcriptional control sequences can be operably linked to coding sequences for a PPN/MG61 fusion protein comprising PPN/MG61 polypeptide fused to a polypeptide which facilitates detection. In these embodiments, the method comprises combining a candidate agent to be tested with a cell comprising a nucleic acid which comprises a PPN/MG61 gene transcriptional regulatory element operably linked to a PPN/MG61 polypeptide-coding sequence; and determining the effect of said agent on PPN/MG61 expression, which determination can be carried out by measuring an amount of PPN/MG61 mRNA, PPN/MG61 polypeptide, or PPN/MG61 fusion polypeptide produced by the cell.

Cell-based assays generally comprise the steps of contacting the cell with an agent to be tested, forming a test sample, and, after a suitable time, assessing the effect of the agent on PPN/MG61 expression. A control sample comprises the same cell without the candidate agent added. PPN/MG61 expression levels are measured in both the test sample and the control sample. A comparison is made between PPN/MG61 expression level in the test sample and the control sample. PPN/MG61 expression can be assessed using conventional assays. For example, when a mammalian cell line is transformed with a construct that results in expression of PPN/MG61, PPN/MG61 mRNA levels can be detected and measured, as described above, or PPN/MG61 polypeptide levels can be detected and measured, as described above. A suitable period of time for contacting the agent with the cell can be determined empirically, and is generally a time sufficient to allow entry of the agent into the cell and to allow the agent to have a measurable effect on PPN/MG61 mRNA and/or polypeptide levels. Generally, a suitable time is between 10 minutes and 24 hours, more typically about 1-8 hours. Methods of measuring PPN/MG61 mRNA levels are known in the art, several of which have been described above, and any of these methods can be used in the methods of the present invention to identify an agent which modulates PPN/MG61 mRNA level in a cell, including, but not limited to, a PCR, such as a PCR employing detectably labeled oligonucleotide primers, a RT-PCR, a real-time RT-PCR, and any of a variety of hybridization assays. Similarly, PPN/MG61 polypeptide levels can be measured using any standard method, several of which have been described herein, including, but not limited to, an immunoassay such as ELISA, for example an ELISA employing a detectably labeled antibody specific for a PPN/MG61 polypeptide.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

The screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature; typically between 4 and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound complexes will then be detected.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known agents may be subjected to directed or random chemical modifications, such as acylation, alkylation, esterification, amidification, etc. to produce structural analogs.

Methods for identifying agents that modulate release of PPN/MG61 from a eukaryotic cell generally comprise contacting a cell that normally produces PPN/MG61 with a test agent, and determining the effect, if any, on release of PPN/MG61.

"Modulation" of release of PPN/MG61 from a eukaryotic cell includes increasing the level and decreasing the level of release of PPN/MG61 from a eukaryotic cell when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of PPN/MG61 mRNA and/or polypeptide following contacting the cell with a candidate agent being tested, compared to a control to which no agent is added, is an indication that the agent modulates release of PPN/MG61 from a eukaryotic cell.

Cell-based assays generally comprise the steps of contacting the cell with an agent to be tested, forming a test sample, and, after a suitable time, assessing the effect of the agent on release of PPN/MG61 from a eukaryotic cell. A control sample comprises the same cell without the candidate agent added. Release of PPN/MG61 from a eukaryotic cell is measured in both the test sample and the control sample. A comparison is made between release of PPN/MG61 from a eukaryotic cell in the test sample and the control sample. Release of PPN/MG61 from a eukaryotic cell can be assessed using conventional assays to measure PPN/MG61 activity. For example, when a mammalian cell line is transformed with a construct that results in expression of PPN/MG61, PPN/MG61 enzymatic activity released from the cell can be detected and measured, as described above, or PPN/MG61 polypeptide levels can be detected and measured, as described above. A suitable period of time for contacting the agent with the cell can be determined empirically, and is generally a time sufficient to allow entry of the agent into the cell (if necessary), or any other interaction with the cell, e.g., with cell-surface components) and to allow the agent to have a measurable effect on PPN/MG61 release. Generally, a suitable time is between 10 minutes and 24 hours, more typically about 1-8 hours.

The invention further provides agents identified using a screening assay of the invention, and compositions comprising the agents, including pharmaceutical compositions. The subject compositions can be formulated using well-known reagents and methods. In some embodiments, compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The nucleic acid compositions and polypeptide compositions of the subject invention also find use as therapeutic agents in situations where one wishes to enhance PPN/MG61 activity in a host, particularly the activity of the subject polypeptides, or to provide PPN/MG61 activity at a particular anatomical site.

In some embodiments, PPN/MG61 is provided in a pharmaceutical composition with a pharmaceutically acceptable excipient.

The subject genes, gene fragments, or the encoded proteins or protein fragments are useful in therapy to treat disorders associated with activity of PPN/MG61. Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are transiently or stably maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature*

356:152-154), where gold microprojectiles are coated with the DNA, then bombarded into skin cells.

In yet other embodiments of the invention, the active agent is an agent that modulates, and generally decreases or down regulates, the expression of the gene encoding the target protein in the host. For example, antisense molecules, small interfering RNA (siRNA), short-hairpin RNA (shRNA), can be used to down-regulate expression of the subject genes in cells. The anti-sense reagent may be antisense oligonucleotides (ODN), particularly synthetic ODN having chemical modifications from native nucleic acids, or nucleic acid constructs that express such antisense molecules as RNA. The ODN, siRNA and shRNA sequences are complementary to the mRNA or cDNA of the targeted gene, and inhibit expression of the targeted gene products. One or a combination of ODN, siRNA and shRNA molecules may be administered, where a combination may comprise multiple different sequences.

Antisense, siRNA and shRNA molecules may be produced by expression of all or a part of the target gene sequence in an appropriate vector, where the transcriptional initiation is oriented such that an antisense strand is produced as an RNA molecule. Alternatively, the antisense, siRNA and shRNA molecules are synthetic.

Antisense oligonucleotides, siRNA and shRNA molecules may be chemically synthesized by methods known in the art. Preferred oligonucleotides are chemically modified from the native phosphodiester structure, in order to increase their intracellular stability and binding affinity. A number of such modifications have been described in the art, that modifications alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The present invention provides various therapeutic methods. In some embodiments, methods of regulating, including modulating and inhibiting, enzymatic activity of the subject proteins are provided. The subject methods find use in the treatment of a variety of different disease conditions, including, but not limited to, cancer; inflammation; disorders amenable to treatment by increasing Wnt signaling and/or angiogenesis, such as ischemic disorders; and thrombosis.

The host, or patient, may be from any mammalian species, e.g. primate sp., particularly humans. Animal models are of interest for experimental investigations, providing a model for treatment of human disease.

As used herein, the term "agent" refers to a substance that modulates a level of enzymatically active subject PPN/MG61. In some embodiments, an agent is one identified by a screening assay of the invention. "Modulating a level of enzymatically active subject PPN/MG61" includes increasing or decreasing enzymatic activity of a subject PPN/MG61; increasing or decreasing a level of enzymatically active PPN/MG61 protein; and increasing or decreasing a level of mRNA encoding enzymatically active subject PPN/MG61. In some embodiments, an agent is PPN/MG61, where the subject PPN/MG61 itself is administered to an individual. In some embodiments, an agent is an antibody specific for PPN/MG61.

Disease conditions amenable to treatment by reducing an activity of PPN/MG61 and/or reducing a level of PPN/MG61 polypeptide or mRNA include those disease conditions associated with or resulting from the promotion of Wnt signaling and/or angiogenesis in a tumor. Thus, the subject methods are useful for reducing Wnt signaling and/or angiogenesis induced tumor. In some embodiments, methods are provided for treating cancer. In some of these embodiments, methods are provided for reducing tumor growth. In other embodiments, methods are provided for reducing release of differentiation factors from the ECM.

Methods of reducing tumor growth, and methods of reducing PPN/MG61 activity, generally comprise administering to an individual an agent that reduces a level of enzymatically active PPN/MG61. An effective amount of an agent reduces the level of enzymatically active PPN/MG61 by at least about 10%, at least about 20%, at least about 30%, at least about 40%, at least about 50%, or more, when compared to a suitable control. An effective amount of an agent reduces tumor growth by at least about 10%, at least about 20%, at least about 30%, at least about 40%, at least about 50%, or more, when compared to a suitable control.

Methods of reducing release of factors, such as growth factors and differentiation factors, from ECM are provided. The methods generally comprise administering to an individual an effective amount of an agent that reduces a level of enzymatically active PPN/MG61, where a reduction in the level of enzymatically active PPN/MG61 results in a reduction of release of factor from the ECM adjacent to or surrounding the tumor.

Differentiation and growth factors include, but are not limited to, Wnt, a fibroblast growth factor (FGF), a heparin-binding EGF-like growth factor, a hepatocyte growth factor, a member of the Wnt family of secreted glycoproteins, vascular endothelial growth factor (VEGF), platelet-derived growth factor (PDGF), a transforming growth factor (TGF), e.g., TGF-β, a bone morphogenetic protein, GM-CSF, and hepatocyte growth factor.

Tumors which may be treated using the methods of the instant invention include carcinomas, e.g. non-small cell lung carcinoma, colon, prostate, breast, melanoma, ductal, endometrial, stomach, pancreactic, mesothelioma, dysplastic oral mucosa, invasive oral cancer, transitional and squamous cell urinary carcinoma, etc.; neurological malignancies, e.g. neuroblastoma, glioblastoma, astrocytoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Whether tumor cell growth is inhibited or reduced can be assessed by any means known in the art, including, but not limited to, measuring tumor size; determining whether tumor cells are proliferating, e.g., by using a $^3$H-incorporation assay; and/or counting tumor cells.

In some embodiments, the invention provides methods of reducing inflammation, comprising increasing a level of enzymatically active PPN/MG61. In some embodiments, the methods comprise administering PPN/MG61 to an individual. In other embodiments, the methods comprise administering an agent (e.g., an agent identified by a screening method described above) to an individual, wherein said agent is one that increases a level of enzymatically active PPN/MG61 in the individual. A therapeutically effective amount an agent is an amount sufficient to remove acyl-moieties from a substantial proportional number of ligands so that inflammation can either be prevented or ameliorated. Thus, "treating" as used herein in the context of inflammation shall mean preventing or ameliorating inflammation and/or symptoms associated with inflammation.

In determining the dose of PPN/MG61 or agents to be administered, it must be kept in mind that one does not wish to completely remove all acyl-groups. In order for a normal healing process to proceed, at least some of the white blood cells or neutrophils must be brought into the tissue in the areas where the wound, infection or disease state is occurring. The amount of the PPN/MG61 or agent administered is adjusted based on the particular needs of the patient while taking into consideration a variety of factors such as the type of disease that is being treated.

The PPN/MG61 and/or agents are useful to treat a wide range of diseases, including diseases such as rheumatoid arthritis, asthma, adult respiratory distress syndrome, sarcoidosis, hypersensitivity pneumonitis multiple sclerosis, allograft rejection, and the spread of lymphomas to cutaneous sites. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

In some embodiments, the invention provides methods for increasing angiogenesis. The methods generally involve administering to a mammal having a condition amenable to treatment by increasing angiogenesis an effective amount of PPN/MG61. In many embodiments, the PPN/MG61 will be administered locally to an anatomical site.

Examples of conditions and diseases amenable to treatment according to the method of the invention include any condition associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, any of a variety of ischemic conditions (e.g., myocardial ischemia, limb ischemia, ischemia associated with stroke), heart attack (myocardial infarction) or other vascular death, stroke, death or loss of limbs associated with decreased blood flow, and the like.

Thus, the invention provides methods of treating an ischemic condition. Administration of an effective amount of PPN/MG61 results in an increase in angiogenesis, and as a result, an increased blood supply to an ischemic tissue. Following administration of PPN/MG61, blood supply (blood flow) to the ischemic tissue is increased by at least about 10%, at least about 20%, at least about 30%, at least about 50%, at least about 75%, or at least about 100%, or more when compared to a suitable control. Whether the blood supply to an ischemic tissue is increased can be measured by any method known in the art, including, but not limited to, thermography; infrared recorder; transcutaneous $PO_2$, transcutaneous $PCO_2$, laser Doppler, Doppler waveform, ankle brachial index, pulse volume recording, toe pressure, duplex waveform, magnetic resonance imaging profile, isotope washout, and NAD/NADH fluorometry. Such methods are well known in the art and have been described in numerous publications.

Whether angiogenesis is increased can be determined using any known assay. Whether angiogenesis is increased can be determined using any method known in the art, including, e.g., stimulation of neovascularization into implants impregnated with relaxin; stimulation of blood vessel growth in the cornea or anterior eye chamber; stimulation of endothelial cell proliferation, migration or tube formation in vitro; and the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51: 1-11), and references cited therein.

As mentioned above, an effective amount of the active agent (e.g., small molecule, anti-PPN/MG61 antibody, or a subject PPN/MG61) is administered to the host, where "effective amount" means a dosage sufficient to produce a desired result. In some embodiments, the desired result is at least a reduction in enzymatic activity of a subject PPN/MG61 as compared to a control. In other embodiments, the desired result is an increase in the level of enzymatically active PPN/MG61 (in the individual, or in a localized anatomical site in the individual), as compared to a control.

Typically, the compositions of the instant invention will contain from less than 1% to about 95% of the active ingredient, preferably about 10% to about 50%. Generally, between about 100 mg and 500 mg will be administered to a child and between about 500 mg and 5 grams will be administered to an adult. Administration is generally by injection and often by injection to a localized area. The frequency of administration will be determined by the care given based on patient responsiveness. Other effective dosages can be readily determined by one of ordinary skill in the art through routine trials establishing dose response curves.

In order to calculate the amount of PPN/MG61, those skilled in the art could use readily available information with respect to the amount of enzyme necessary to remove a given amount of PPN/MG61. For example, if a given enzyme has an activity such that one unit of the enzyme removes 1 micromole/min. of $SO_4$ from a substrate at physiological pH, then one would administer from 1 to 10 units intravenously to a 70 kg human for therapeutic purposes. The amount of an agent necessary to increase a level of enzymatically active PPN/MG61 can be calculated from in vitro experimentation. For example, by calculating the amount of agent necessary to increase removal of acyl-groups from a given amount of substrate and estimating the amount of such substrate (or its in vivo equivalent) within the area to be treated, an amount of agent to be administered can be determined. The amount of agent will, of course, vary depending upon the particular agent used.

In the subject methods, the active agent(s) may be administered to the host using any convenient means capable of resulting in the desired inhibition of PPN/MG61 activity. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the chlorate/selenate and/or PPN/MG61 adequate to achieve the desired state in the subject being treated.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense, siRNA or shRNA composition, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the therapeutic DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The PPN/MG61 and agent of the present invention can be used by themselves, with each other, or in combination with pharmaceutically acceptable excipient materials as described above.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Advantageously The PPN/MG61 and agent of the present invention can be administered to a subject with a malignancy with at least one other non-platinum and platinum containing anti-tumor agent. For example, but not to limit the present invention, an anti-PPN/MG61 compound can be administered in a dosing regimen with a cytotoxic compound, such as a DNA alkylating agent, or with an anti-angiogenic compound, or anti-tumor agents (compound or monoclonal antibody). Preferred anti-tumor agents are selected from the group consisting of cladribine (2-chloro-2'-deoxy-(beta)-D-adenosine), Chlorambucil (4-[bis(2-chlorethyl)amino]ben-zenebutanoic acid), DTIC-Dome (5-(3,3-dimethyl-1-triaz-eno)-imidazole-4-carboxamide), platinum chemotherapeutics and nonplatinum chemotherapeutics. Platinum containing anti-tumor agents includes, but is not limited to, cisplatin (cis-dichlorodiamineplatinum). Non-platinum containing anti-tumor agents includes, but is not limited to, cyclophosphamide, fluorouracil, epirubicin, methotrexate, vincristine, doxorubicin, bleomycin, and etoposide. Each anti-tumor agent is administered within therapeutically effective amounts, which are well known in the art, and vary based on the agent used, the type of malignancy, and other conditions.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

PPN/MG61 Expression in Human Normal and Cancer Cell Lines

We studied PPN/MG61 mRNA expression in a variety of human cancer cell lines as well as normal human primary cells by using semi-quantitative RT-PCR (FIG. 1). The human cancer cell lines that we examined include non-small-cell lung cancer (NSCLC) (A549, H460, H838, H1299 and H1703), breast cancer (MCF-7, BT474 and HuL 100), malignant plural mesothelioma (H513, H2052, H290, MS-1 and H28), colon cancer (SW480 and HCT116), head and neck cancer (U87), cervical cancer (Hela), sarcoma (Mes-SA, Saos-2 and A204). The normal human primary cells that we examined were small airway epithelial cells (SAEC), bronchial epithelial cells (NHBE) and normal mesothelial cells (LP-9). Total RNA from each cell type was prepared and same amount total RNA was used in each RT-PCR analysis. A housekeeping gene GAPDH was amplified in all samples and used as internal and loading controls. In all three normal human cell cultures, no expression of PPN/MG61 mRNA was noticed (FIG. 1). In contrast, high-level PPN/MG61 mRNA expression was observed in all human cancer cell lines that we tested (FIG. 1). These results suggest that PPN/MG61 is highly expressed in all human cancer cell lines, but not in normal human cells examined.

Example 2

PPN/MG61 Expression in Human Normal and Cancer Lung Tissue Samples

Figure 2:
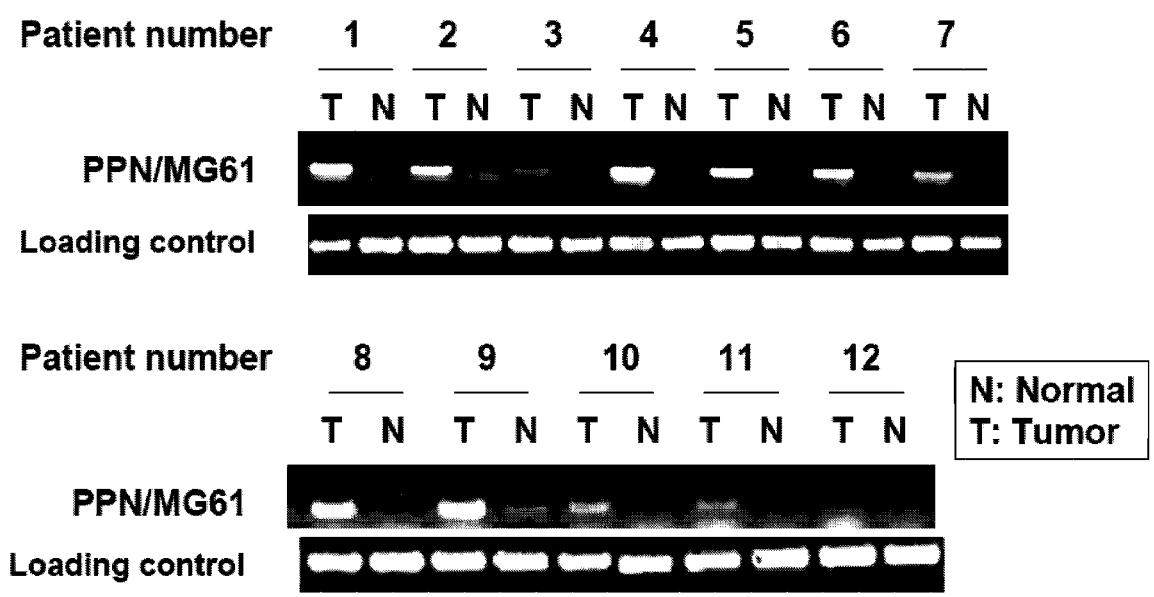
FIG. 2. PPN/MG61 expression in human normal and cancer lung tissue samples. RT-PCR analysis of PPN/MG61 mRNA levels in primary non-small-cell lung cancer (NSCLC) tissue samples. Total RNA was prepared from freshly resected cancer and autologous matched normal lung tissues of the same patients.

We next examined PPN/MG61 mRNA expression in primary non-small-cell lung cancer (NSCLC) tissue samples and their matched normal lung samples of the same patients by using semi-quantitative RT-PCR (FIG. 2). Fresh lung cancer tissue and adjacent normal lung tissue from patients undergoing curative primary resection of their tumors were collected at the time of surgery, and immediately snap-frozen in liquid nitrogen. These tissue samples were kept at −170° C. in a liquid nitrogen freezer until use.

Total RNA was then prepared from those freshly resected lung cancer and autologous matched normal lung tissues of the same patients, and same amount of total RNA was used in each RT-PCR analysis. In twenty-four matched human non-cancerous and cancerous lung tissue samples that we examined, we found that almost all (twenty-three) lung cancer tissue samples (95.8%) over-expressed PPN/MG61 mRNA compared to their matched normal lung tissue samples (FIG. 2). Only minimal or no PPN/MG61 expression was observed in all normal lung samples.

Example 3

Figure 3:
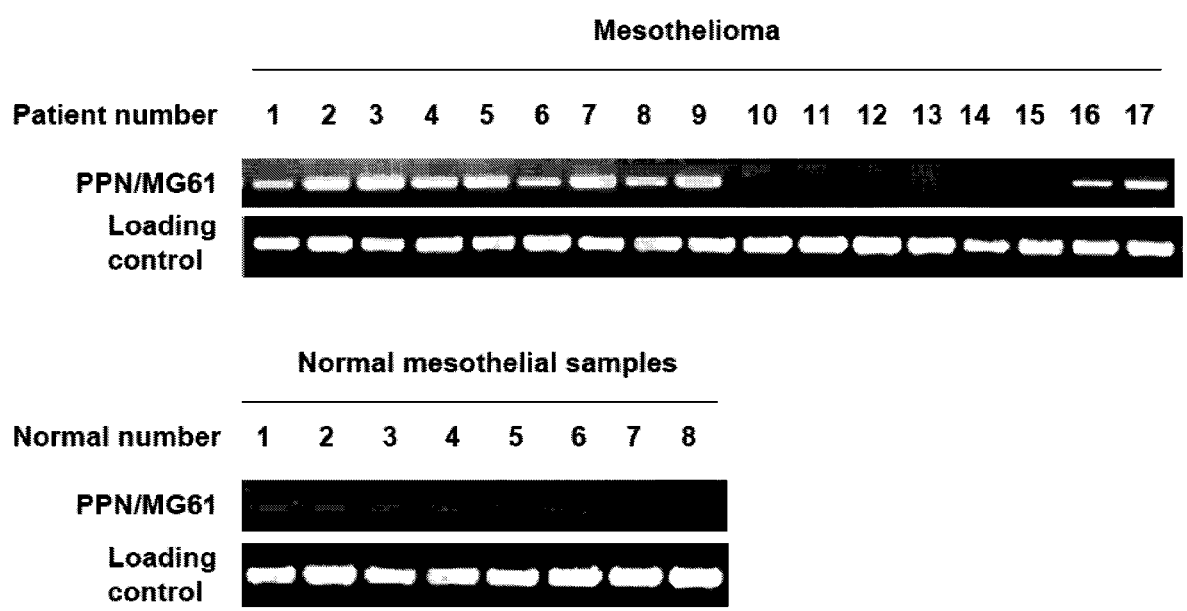
FIG. 3. RT-PCR analysis of PPN/MG61 expression levels in primary human mesothelioma tissue samples. Total RNA was prepared from freshly resected cancer patients.

RT-PCR Analysis of PPN/MG61 Expression Levels in Primary Human Mesothelioma Tissue Samples We also examined PPN/MG61 mRNA expression in primary mesothelioma tissue and normal plural tissue samples by using semi-quantitative RT-PCR (FIG. 3). Fresh mesothelioma tissue and adjacent normal plural tissue from patients undergoing curative primary resection of their tumors were collected at the time of surgery, and immediately snap-frozen in liquid nitrogen. These tissue samples were kept at −170° C. in a liquid nitrogen freezer until use. Total RNA was then prepared from those freshly resected mesothelioma and normal tissues of the patients, and same amount of total RNA was used in each RT-PCR analysis. In all cancerous mesothelioma tissue samples that we examined, we found that 64.7% (11 of 17) mesothelioma tissue samples over-expressed PPN/MG61 mRNA (FIG. 3). No PPN/MG61 expression was observed in all normal samples (FIG. 3).

Example 4

Figure 4:
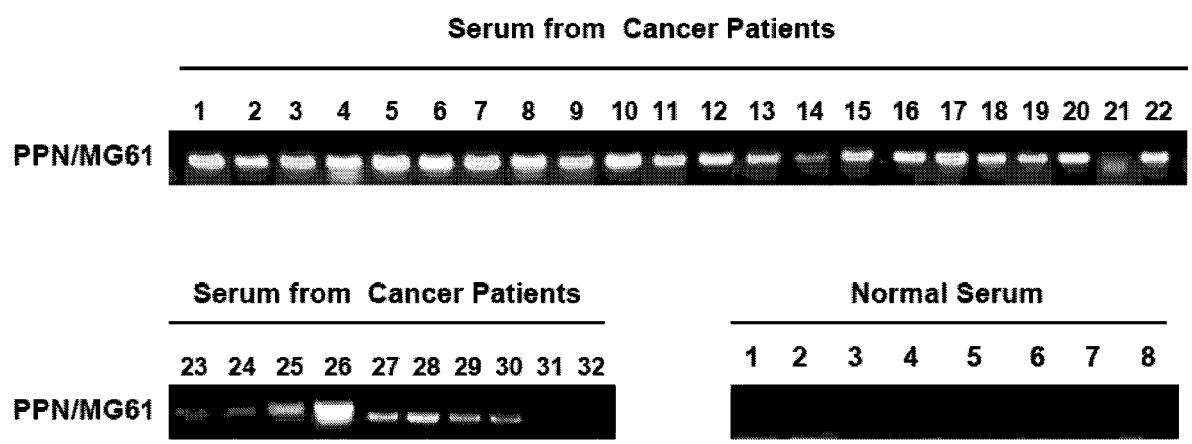
FIG. 4. RT-PCR analysis of PPN/MG61 mRNA levels in normal human serum and serum samples from cancer patients, including NSCLC, mesothelioma, colon cancer, melanoma, renal cancer, esophageal cancer, thyroid cancer, sarcoma, ovarian cancer. Total RNA was prepared from serum samples and was used in the reactions.

RT-PCR Analysis of PPN/MG61 mRNA Levels in Normal Human Serum and Serum Samples from Cancer Patients Next we examined whether the frequent over-expression of PPN/MG61 mRNA could be detected in serum samples of cancer patients. The serum samples were collected according to the standard procedure from a variety of cancer patients, including NSCLC, mesothelioma, colon cancer, melanoma, renal cancer, esophageal cancer, thyroid cancer, sarcoma and ovarian cancer. Total RNA was then prepared from the serum samples within 3 hours after the serum collection and was used in the RT-PCR reactions (FIG. 4). In thirty-two samples from cancer patient serum that we examined, we found that 93.8% (30 of 32) samples over-expressed PPN/MG61 mRNA (FIG. 4). No PPN/MG61 expression was observed in all eight normal controls where total RNA was prepared from serum of eight different normal people (FIG. 4).

Figure 5:
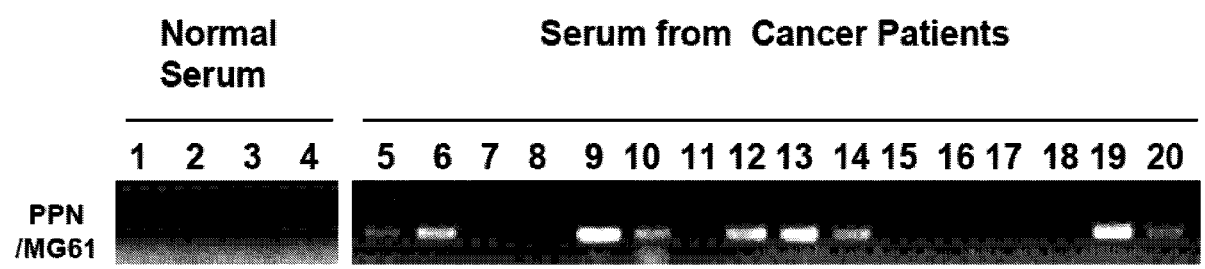
FIG. 5. RT-PCR analysis of PPN/MG61 mRNA levels in normal human serum and serum samples from cancer patients. Serum samples were not treated and were used directly in the reactions.

In a second experiment, we tested whether the over-expression of PPN/MG61 mRNA can be detected directly from the serum samples of cancer patients without total RNA isolation by using RT-PCR (FIG. 5). In this experiment, all serum samples without further treatment after the collection were directly added into the RT-PCR reactions (1 μl serum in 25 μl reaction systems). The experiment was performed within 3 hours after the serum collection. After 36 cycles, we detected over-expression of PPN/MG61 mRNA in 10 of 16 (62.5%) serum samples of cancer patients. In contrast, no PPN/MG61 expression was observed in all four normal serum samples under the same experimental condition (FIG. 5).

Figure 6:
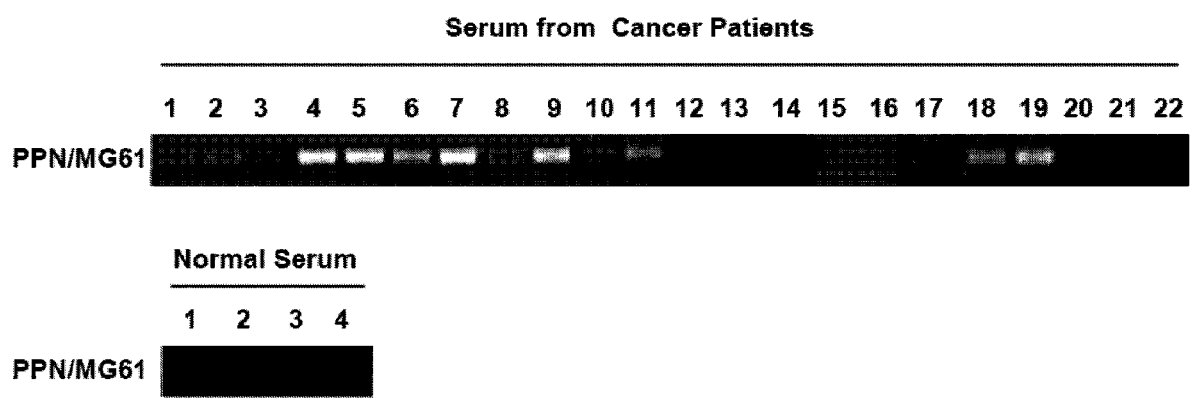
FIG. 6. RT-PCR analysis of PPN/MG61 mRNA levels in normal human serum and serum samples from cancer patients. Serum samples were heat-treated before used in the reactions.

In a third experiment, we tested whether the over-expression of PPN/MG61 mRNA can be detected directly from heat-treated serum samples of cancer patients without total RNA isolation by using RT-PCR (FIG. 6). In this experiment, all serum samples were heated at 75° C. for approximately 10 minutes after the serum collection and were then added into the RT-PCR reactions (1 μl heat-treated serum in 25 μl reaction systems). The experiment was also performed within 3 hours after the serum collection. After 36 cycles, we detected over-expression of PPN/MG61 mRNA in 12 of 22 (54.5%) serum samples of cancer patients. In contrast, no PPN/MG61 expression was observed in all four normal serum samples under the same experimental condition (FIG. 6). In summary, we were able to detect over-expression of PPN/MG61 mRNA directly in serum samples collected from cancer patients at high frequency (over 55%) by using different approaches. However, we did not detect PPN/MG61 expression in all normal serum samples collected from different non-cancerous people under the same experimental conditions.

Example 5

Figure 7A:
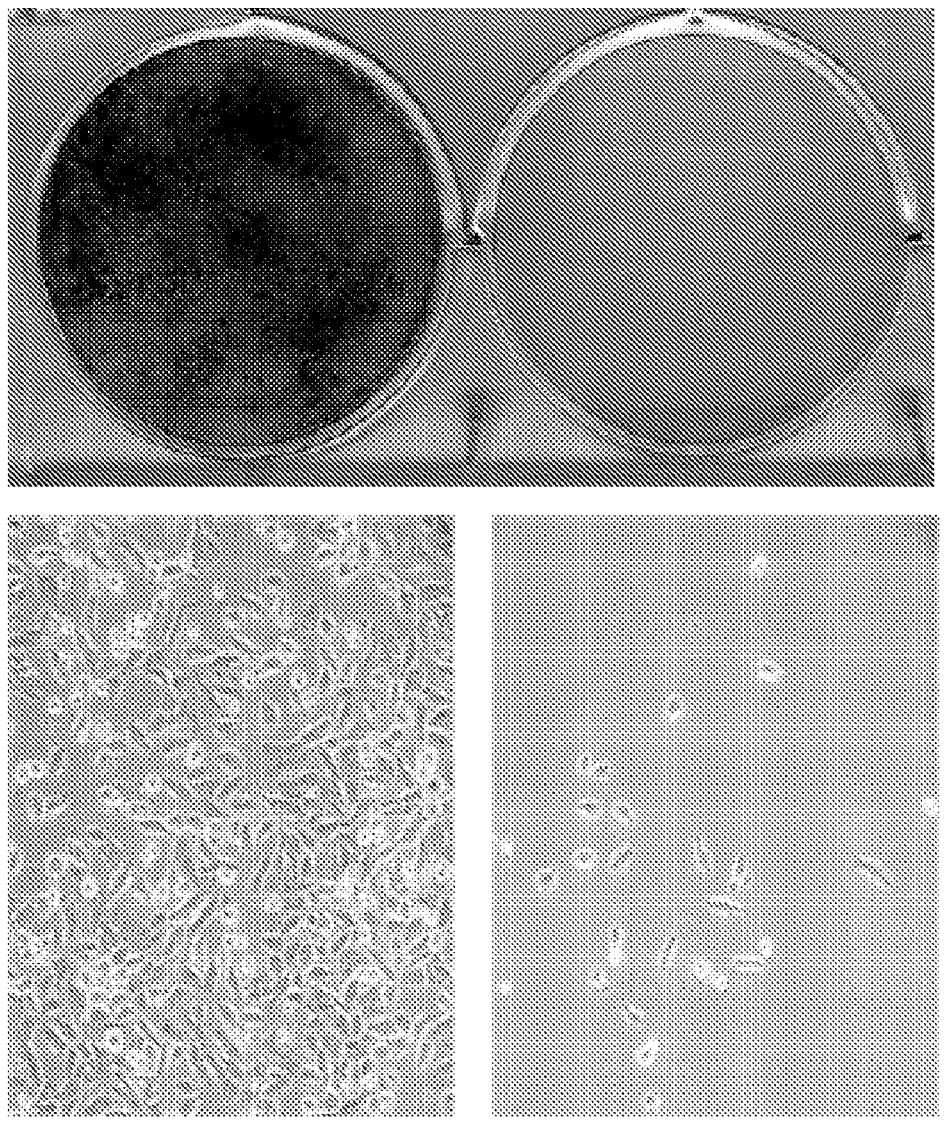
FIG. 7. siRNA targeting PPN/MG61 induces apoptosis in NSCLC cell line H460. A) The H460 cells were stained by using 0.5% Crystal Violet after 100 nM PPN/MG61 siRNA treatment (after 6 days). B) Flow cytometry analysis (Annexin V-FITC and PI staining) of apoptosis induced by PPN/MG61 siRNA. From left to right, H460 cancer cells were treated with 100 nM of non-silencing control siRNA and PPN/MG61 siRNA, respectively. C) RT-PCR and Western analysis after PPN/MG61 siRNA treatment in H460 cells. Non-silencing siRNA was used as control. Beta-actin was used as loading control.
Figure 7B:
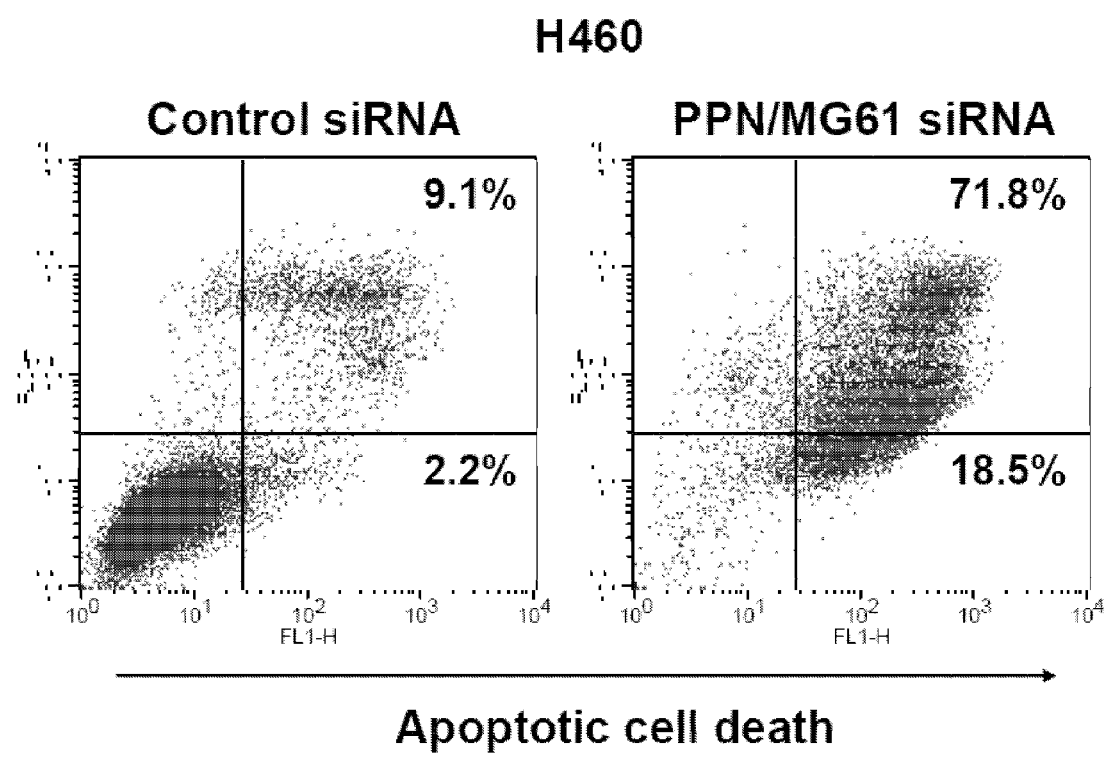
Figure 7C:
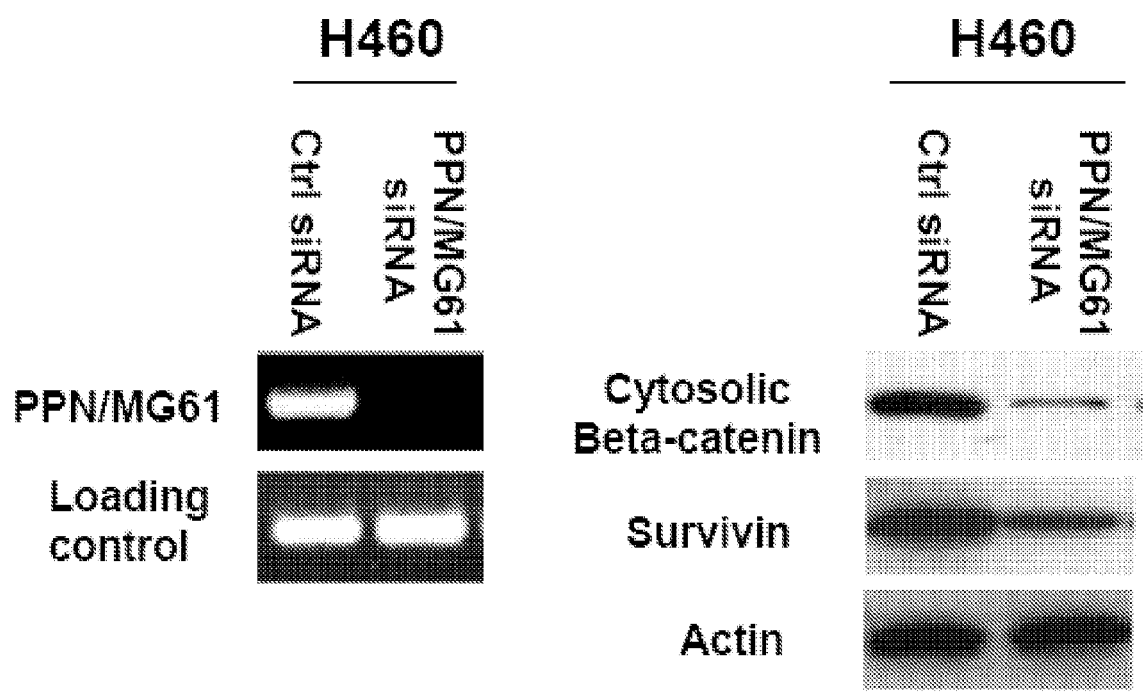
Figure 8A:
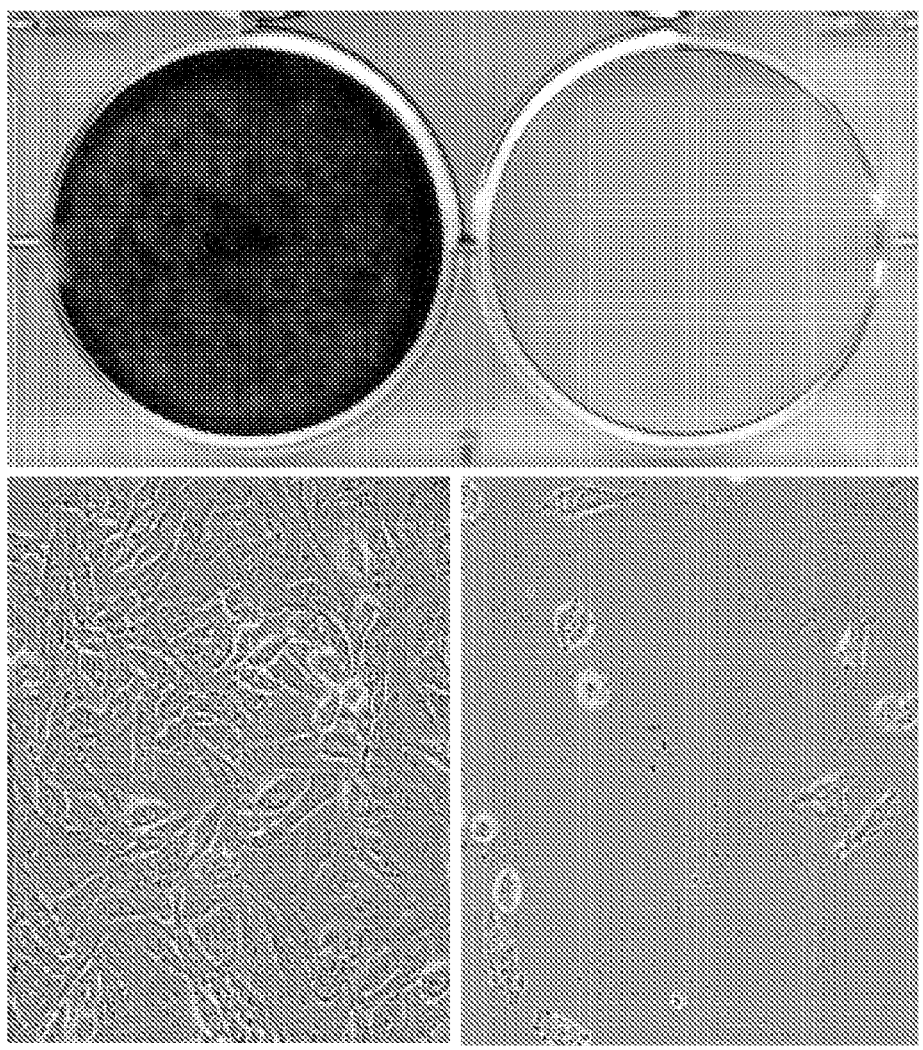
FIG. 8. siRNA targeting PPN/MG61 induces apoptosis and blocks Wnt/beta-Catenin signal transduction in NSCLC cell line H1703. A) The H1703 cells were stained by using 0.5% Crystal Violet after 100 nM PPN/MG61 siRNA treatment (after 4 days). B) Flow cytometry analysis (Annexin V-FITC and PI staining) of apoptosis induced by PPN/MG61 siRNA. From left to right, H1703 cancer cells were treated with 100 nM of non-silencing control siRNA and PPN/MG61 siRNA, respectively. C) RT-PCR and Western analysis after PPN/MG61 siRNA treatment in H1703 cells. Non-silencing siRNA was used as control. Beta-actin was used as loading control.
Figure 8B:
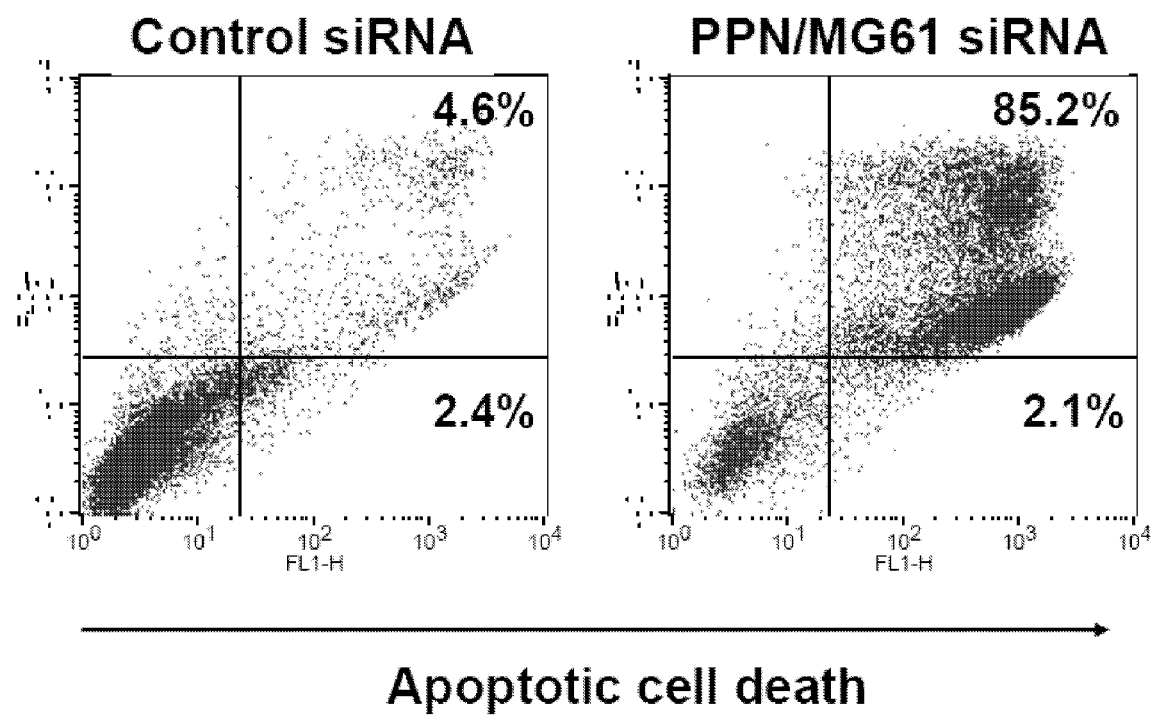
Figure 8C:
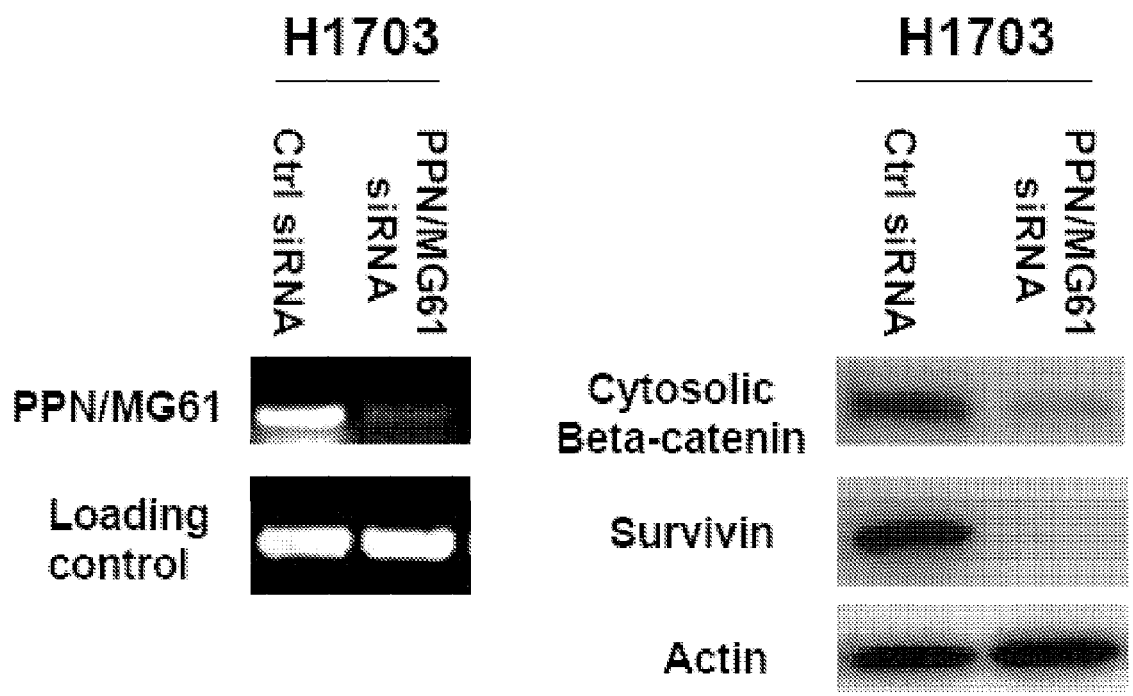
Figure 9A:
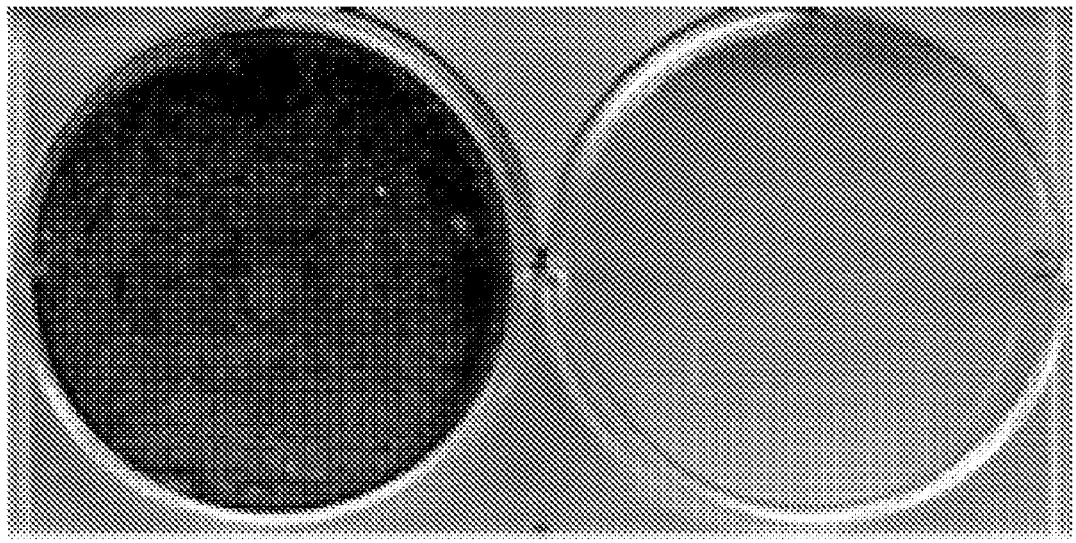
FIG. 9. siRNA targeting PPN/MG61 induces apoptosis and blocks Wnt/beta-Catenin signal transduction in NSCLC cell line A549. A) Flow cytometry analysis (Annexin V-FITC and PI staining) of apoptosis induced by PPN/MG61 siRNA. From left to right, A549 cancer cells were treated with 100 nM of non-silencing control siRNA and PPN/MG61 siRNA, respectively. B) RT-PCR and Western analysis after PPN/MG61 siRNA treatment in A549 cells. Non-silencing siRNA was used as control.
Figure 9B:
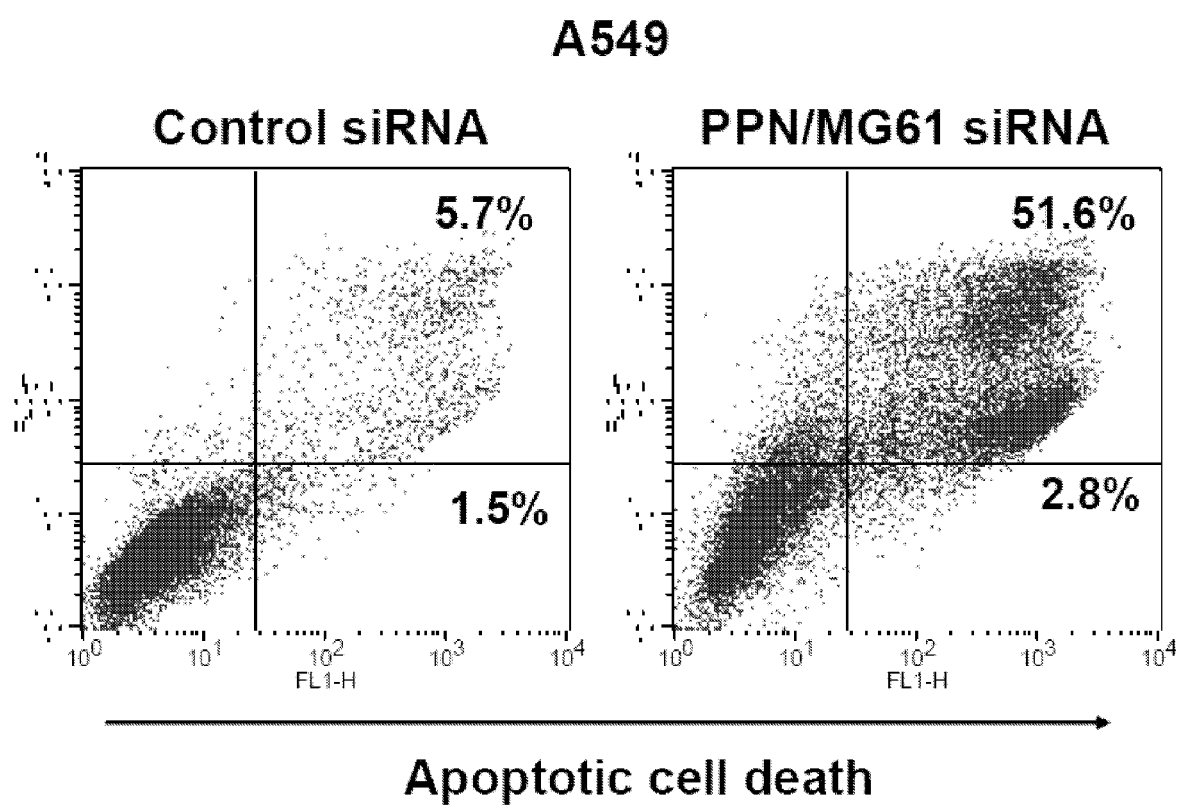
Figure 9C:
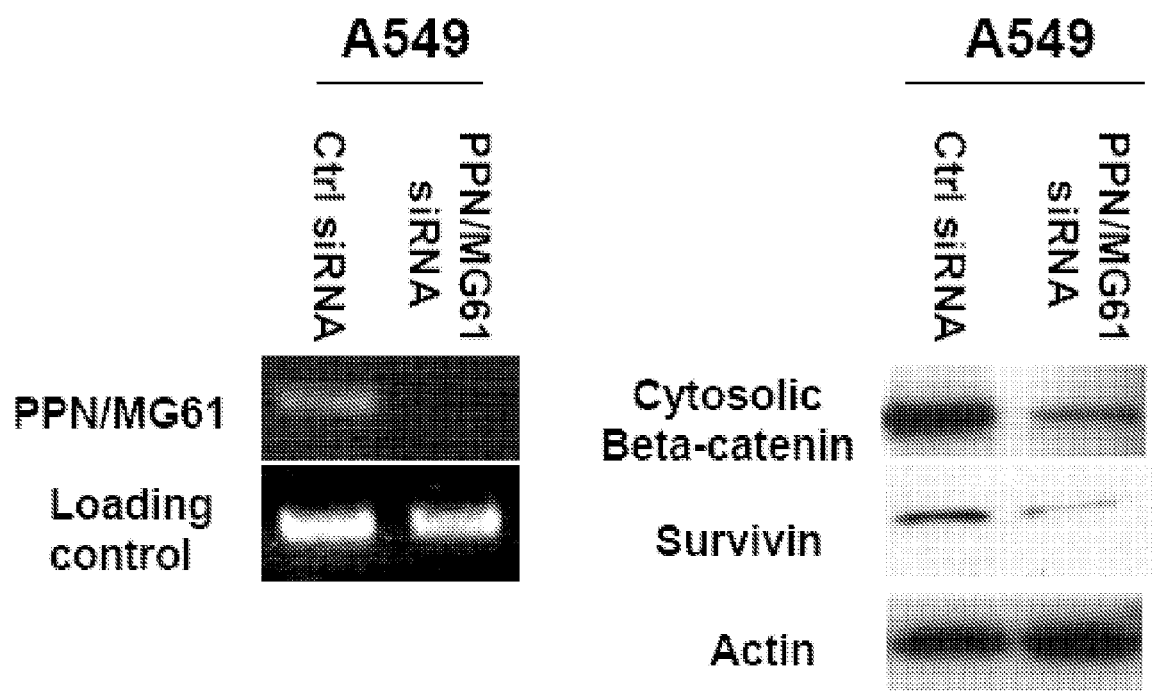

PPN/MG61 siRNA Induces Apoptosis and Blocks Wnt/Beta-Catenin Signaling in Non-Small-Cell Lung Cancer (NSCLC) Cells To further understand the role that PPN/MG61 plays during the development of human NSCLC, we examined whether PPN/MG61 was necessary for NSCLC cell survival and proliferation by knocking down the PPN/MG61 expression using RNA interference (RNAi). Small interfering RNA (siRNA) was designed and chemically synthesized at Qiagen, Inc. RNAi was then carried out by following the protocol described by Elbashir et al (2001). Treatment with PPN/MG61 siRNA for 4-6 days induced significant cell death in NSCLC cell lines expressing PPN/MG61 that we tested (FIGS. 7A, and 8A, P<0.001). We saw no noticeable effect, however, in cell lines after control siRNA treatment. We further found that the cell killing was largely due to induction of apoptosis in these cell lines. Significant apoptosis was induced by 100 nM PPN/MG61 siRNA, and no apoptosis was induced by non-silencing siRNA control (100 nM) (P<0.01) (FIGS. 7B, 8B, and 9B). We also confirmed the silencing of PPN/MG61 expression after PPN/MG61 siRNA treatments (100 nM for 72 hrs) by RT-PCR analysis (FIGS. 7C, 8C, and 9C). Non-silencing siRNA served as control (100 nM for 72 hrs). To examine whether the apoptotic effects correlated with the inhibition of Wnt signaling, we showed that expression levels of cytosolic β-Catenin and Survivin were down-regulated after PPN/MG61 siRNA treatment (FIGS. 7C, 8C, and 9C). β-Actin was used as loading control in all experiments.

Example 6

Figure 10A:
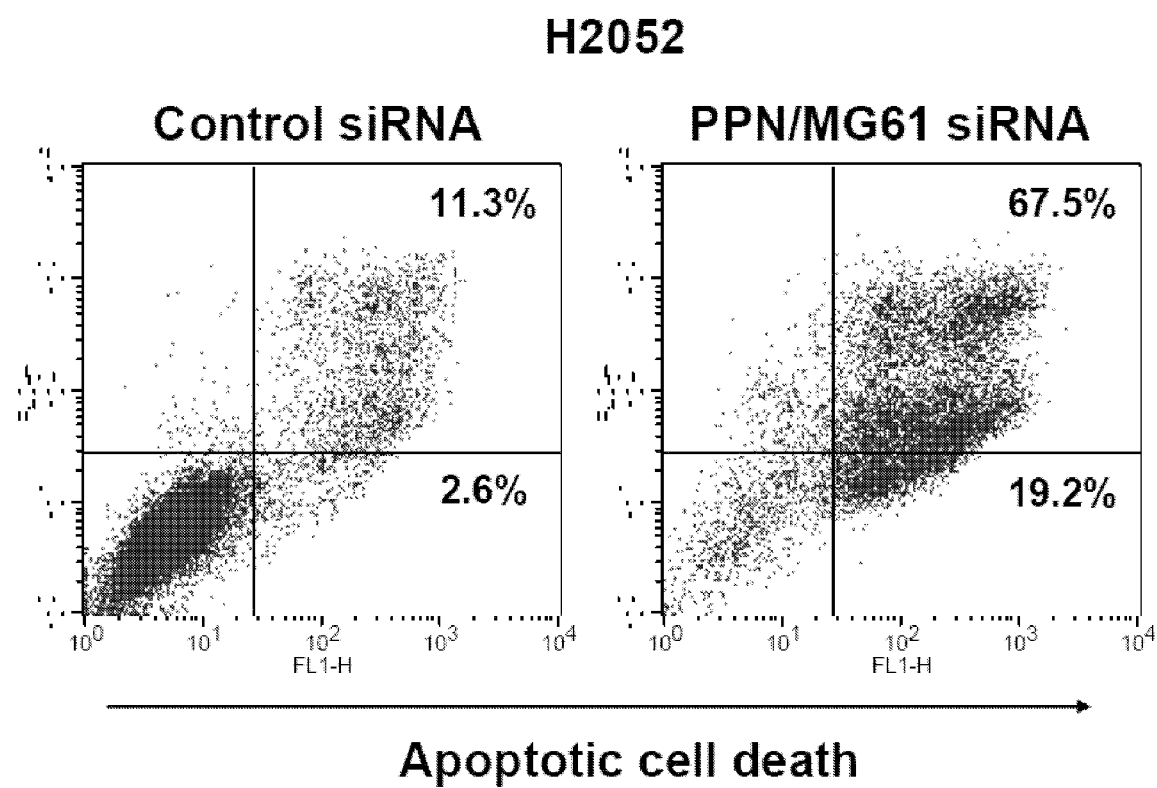
FIG. 10. siRNA targeting PPN/MG61 induces apoptosis and blocks Wnt/beta-Catenin signal transduction in mesothelioma cell line H2052. A) Flow cytometry analysis (Annexin V-FITC and PI staining) of apoptosis induced by PPN/MG61 siRNA. From left to right, H2052 cancer cells were treated with 100 nM of non-silencing control siRNA and PPN/MG61 siRNA, respectively. B) RT-PCR and Western analysis after PPN/MG61 siRNA treatment in H2052 cells. Non-silencing siRNA was used as control. Beta-actin was used as loading control.
Figure 10B:
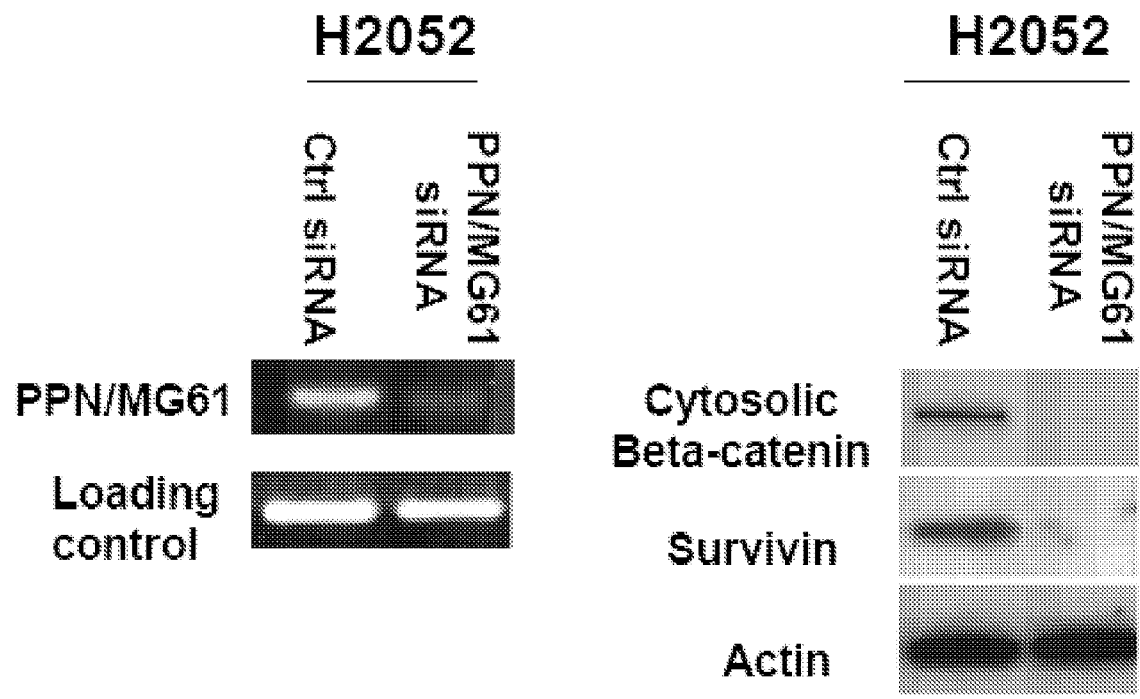

PPN/MG61 siRNA Induces Apoptosis and Blocks Wnt/Beta-Catenin Signaling in Mesothelioma Cells To further understand the role that PPN/MG61 plays during the development of human mesothelioma, we next examined whether PPN/MG61 was necessary for mesothelioma cell survival and proliferation by knocking down the PPN/MG61 expression using RNAi. siRNA used was the same as the ones mentioned above. RNAi was then carried out by following the protocol described by Elbashir et al (2001). Treatment with PPN/MG61 siRNA for 4-6 days induced apoptosis in a mesothelioma cell line expressing PPN/MG61 that we tested (FIG. 10). Significant apoptosis was induced by 100 nM PPN/MG61 siRNA, and no apoptosis was induced by non-silencing siRNA control (100 nM) (P<0.01) (FIG. 10A). We also confirmed the silencing of PPN/MG61 expression after PPN/MG61 siRNA treatments (100 nM for 72 hrs) by RT-PCR analysis (FIG. 10B). Non-silencing siRNA served as control (100 nM for 72 hrs). To examine whether the apoptotic effects correlated with the inhibition of Wnt signaling, we showed that expression levels of cytosolic β-Catenin and Survivin were down-regulated after PPN/MG61 siRNA treatment (FIG. 10B). Again, β-Actin was used as loading control in all experiments.

Example 7

Figure 11A:
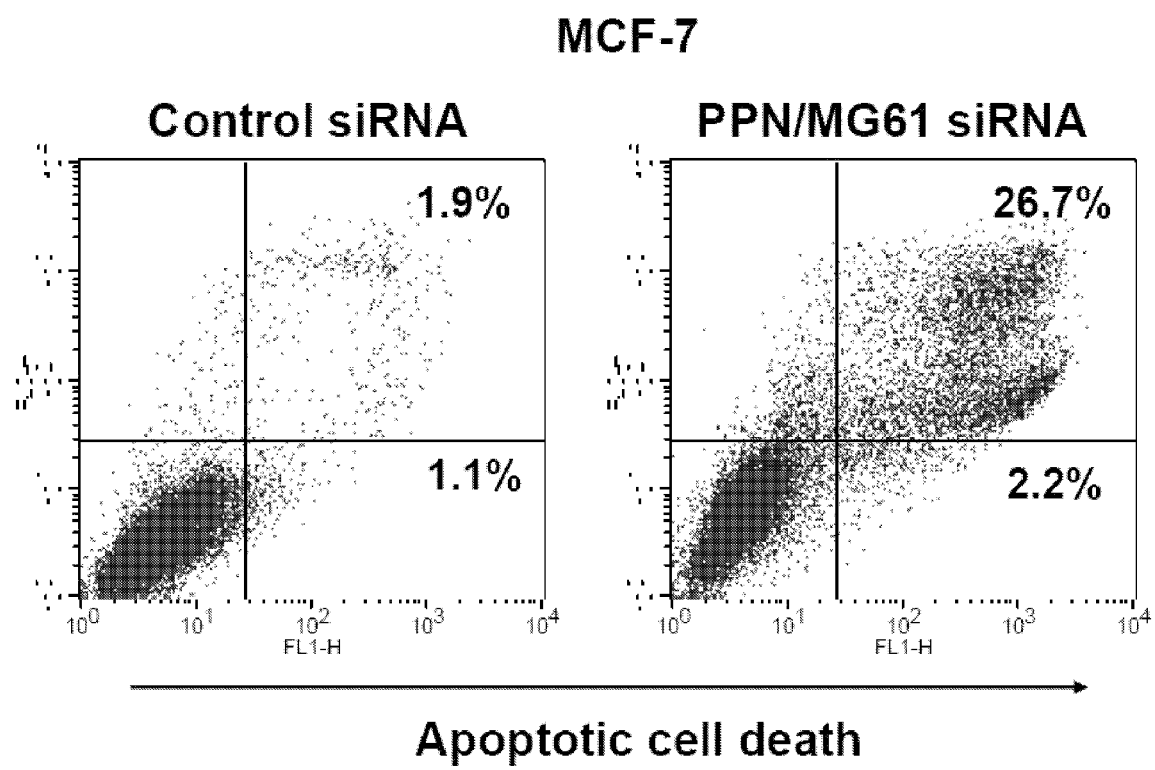
FIG. 11. siRNA targeting PPN/MG61 induces apoptosis and blocks Wnt/beta-Catenin signal transduction in breast cancer cell line MCF-7. A) Flow cytometry analysis (Annexin V-FITC and PI staining) of apoptosis induced by PPN/MG61 siRNA. From left to right, MCF-7 breast cancer cells were treated with 100 nM of non-silencing control siRNA and PPN/MG61 siRNA, respectively. B) RT-PCR and Western analysis after PPN/MG61 siRNA treatment in MCF-7 cells. Non-silencing siRNA was used as control. Beta-actin was used as loading control.
Figure 11B:
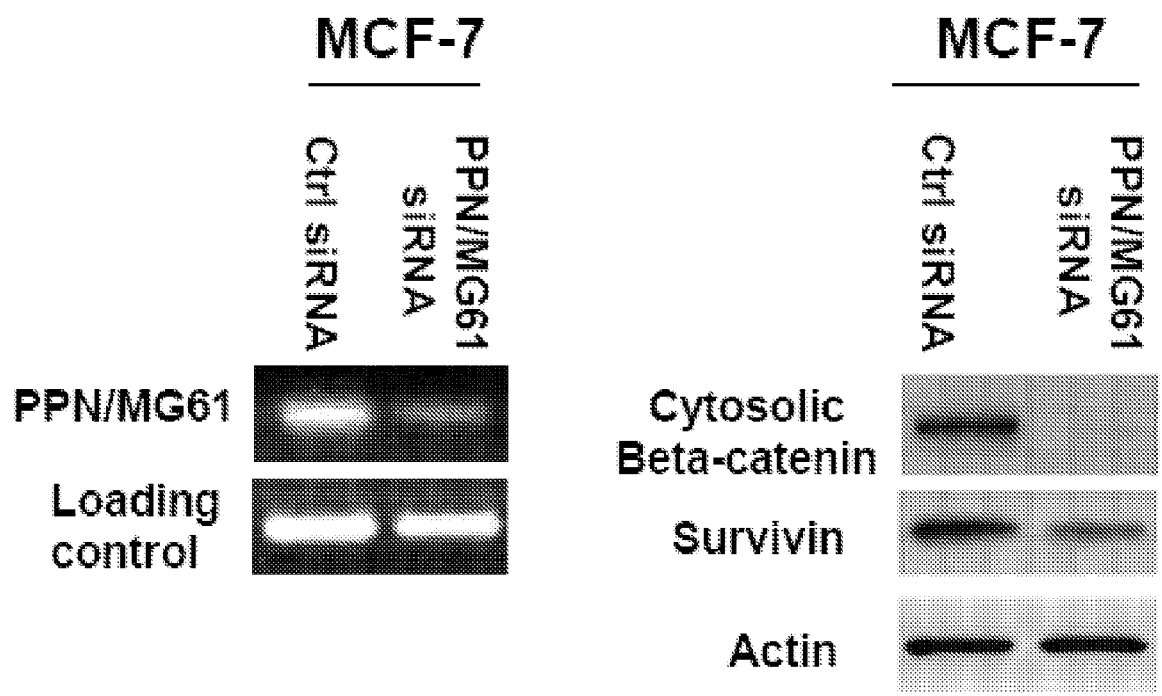

PPN/MG61 siRNA Induces Apoptosis and Blocks Wnt/Beta-Catenin Signaling in Breast Cancer Cells To further understand the role that PPN/MG61 plays during the development of human breast cancer, we also examined whether PPN/MG61 was necessary for breast cancer cell survival and proliferation by knocking down the PPN/MG61 expression using RNAi. siRNA used was the same as the ones mentioned above. RNAi was then carried out by following the protocol described by Elbashir et al (2001). Treatment with PPN/MG61 siRNA for 4-6 days induced apoptosis in a breast cancer cell line expressing PPN/MG61 that we tested (FIG. 11). Significant apoptosis was induced by 100 nM PPN/MG61 siRNA, and no apoptosis was induced by non-silencing siRNA control (100 nM) (P<0.01) (FIG. 11A). We also confirmed the silencing of PPN/MG61 expression after PPN/MG61 siRNA treatments (100 nM for 72 hrs) by RT-PCR analysis (FIG. 11B). Non-silencing siRNA served as control (100 nM for 72 hrs). To examine whether the apoptotic effects correlated with the inhibition of Wnt signaling, we showed that expression levels of cytosolic β-Catenin and Survivin were down-regulated after PPN/MG61 siRNA treatment (FIG. 11B). Again, β-Actin was used as loading control in all experiments.

Example 8

Figure 12A:
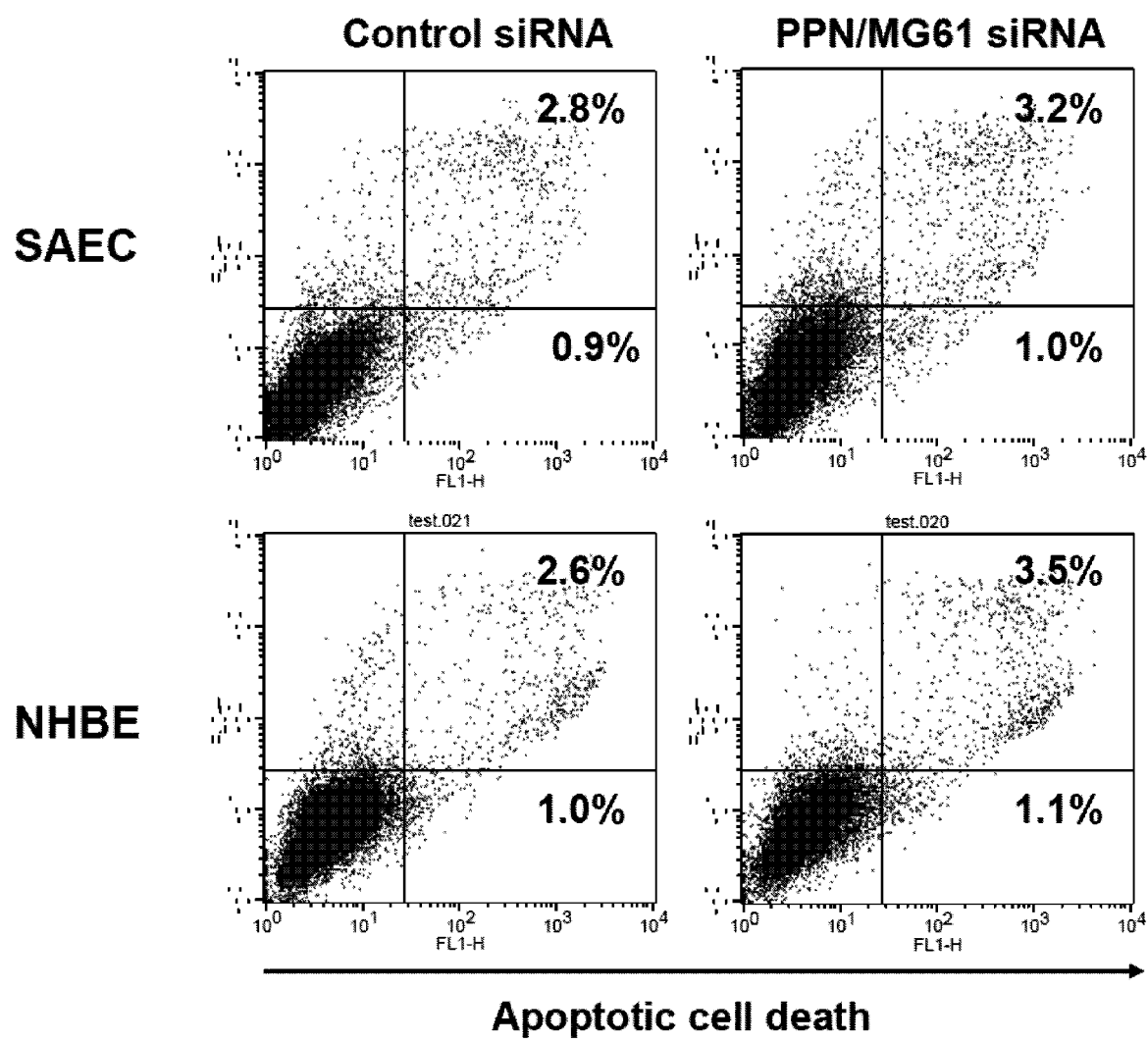
FIG. 12. Negative control experiments: siRNA targeting PPN/MG61 does not induces apoptosis and blocks Wnt/beta-Catenin signal transduction in normal cell cultures SAEC and NHBE lacking PPN/MG61 expression. A) Flow cytometry analysis (Annexin V-FITC and PI staining). From left to right, SAEC (top) and NHBE (bottom) were treated with 100 nM of non-silencing control siRNA and PPN/MG61 siRNA, respectively. B) RT-PCR and Western analysis after PPN/MG61 siRNA treatment in normal cells (SAEC and NHBE). Non-silencing siRNA was used as control. Beta-actin was used as loading control.
Figure 12B:
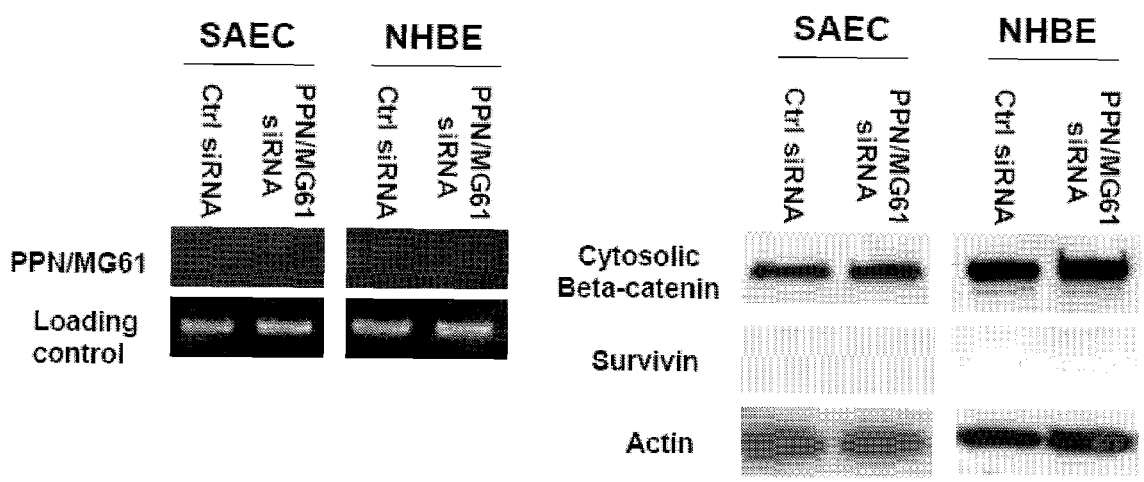

Negative Control: PPN/MG61 siRNA does not Induces Apoptosis and Blocks Wnt/Beta-Catenin Signaling in Normal Cells Lacking PPN/MG61 Expression To examine the effect of PPN/MG61 siRNA in normal cells where no PPN/Mg61 expression was observed, we transfected the PPN/MG61 siRNA into two different normal cell cultures lacking PPN/MG61 expression (FIG. 12). We did not observe significant apoptosis induction after the treatment of 100 nM PPN/MG61 siRNA for 4-6 days when compared to non-silencing siRNA control (100 nM) (FIG. 12A). No expression of PPN/MG61 before and after the siRNA treatment in these normal cells by semi-quantitative RT-PCR (100 nM for 72 hrs) (FIG. 12B). Non-silencing siRNA served as control (100 nM for 72 hrs). We also found no inhibition of Wnt signaling by confirming that expression levels of both cytosolic β-Catenin and Survivin did not change after PPN/MG61 siRNA treatment (FIG. 12B). Again, β-Actin was used as loading control in all experiments. Taken together, our results indicate that inhibition of PPN/MG61 can specifically and selectively induce apoptosis in cancer cells that express PPN/MG61, but not in normal cells that do not express PPN/MG61. These results also suggest a strong linkage between PPN/MG61 function and cancer cell survival.

Example 9

Multiple Alignment of a Conserved Region in the Membrane-Bound O-acyltransferase Family Only selected proteins are shown (FIG. 13). Species and enzyme names are abbreviated: AT, *Arabidopsis thaliana*; BS, *Bacillus subtilis*; CE, *Caenorhabditis elegans*; DM, *Drosophila melanogaster*; HS, *Homo sapiens*; MM, *Mus musculus*; PA, *Pseudomonas aeruginosa*; SA, *Staphylococcus aureus*; SC, *Saccharomyces cerevisiae*; SI, *Simmondsia chinensis*; TP, *Treponema pallidum*; ACAT, cholesterol acyltransferase; DGAT, diacylglycerol O-acyltransferase; Wax-Syn, wax synthase. Invariant residues and conservative substitutions in >50% of the sequences are shown on black and gray background, respectively, and highly conserved polar residues are shown on a colored background. The numbers at the left of the alignment indicate the position in the sequence, the black bar on top indicates a long hydrophobic region.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A kit for detecting the presence and level of PPN/MG61 polynucleotide in a biological sample, wherein the kit comprises a nucleic acid consisting of the nucleic acid sequence of SEQ ID NO:3.

2. An isolated nucleic acid consisting of the nucleic acid sequence of SEQ ID NO:3.

3. A composition comprising the isolated nucleic acid of claim 2.

* * * * *

SEQUENCE LISTING

<160> NUMBER OF SEQ ID NOS: 14

<210> SEQ ID NO 1
<211> LENGTH: 461
<212> TYPE: PRT
<213> ORGANISM: human

<400> SEQUENCE: 1

```
Met Ala Thr Phe Ser Arg Gln Glu Phe Phe Gln Gln Leu Leu Gln Gly
1               5                   10                  15

Cys Leu Leu Pro Thr Ala Gln Gln Gly Leu Asp Gln Ile Trp Leu Leu
            20                  25                  30

Leu Ala Ile Cys Leu Ala Cys Arg Leu Leu Trp Arg Leu Gly Leu Pro
        35                  40                  45

Ser Tyr Leu Lys His Ala Ser Thr Val Ala Gly Gly Phe Phe Ser Leu
    50                  55                  60

Tyr His Phe Phe Gln Leu His Met Val Trp Val Val Leu Leu Ser Leu
65                  70                  75                  80

Leu Cys Tyr Leu Val Leu Phe Leu Cys Arg His Ser Ser His Arg Gly
                85                  90                  95

Val Phe Leu Ser Val Thr Ile Leu Ile Tyr Leu Leu Met Gly Glu Met
            100                 105                 110

His Met Val Asp Thr Val Thr Trp His Lys Met Arg Gly Ala Gln Met
        115                 120                 125

Ile Val Ala Met Lys Ala Val Ser Leu Gly Phe Asp Leu Asp Arg Gly
    130                 135                 140

Glu Val Gly Thr Val Pro Ser Pro Val Glu Phe Met Gly Tyr Leu Tyr
145                 150                 155                 160

Phe Val Gly Thr Ile Val Phe Gly Pro Trp Ile Ser Phe His Ser Tyr
                165                 170                 175

Leu Gln Thr Val Gln Gly Arg Pro Leu Ser Cys Arg Trp Leu Gln Lys
            180                 185                 190

Val Ala Arg Ser Leu Ala Leu Ala Leu Leu Cys Leu Val Leu Ser Thr
        195                 200                 205

Cys Val Gly Pro Tyr Leu Phe Pro Tyr Phe Ile Pro Leu Asn Gly Asp
    210                 215                 220

Arg Leu Leu Arg Asn Lys Lys Arg Lys Ala Arg Gly Thr Met Val Arg
225                 230                 235                 240
```

```
Trp Leu Arg Ala Tyr Glu Ser Ala Val Ser Phe His Phe Ser Asn Tyr
            245                 250                 255

Phe Val Gly Phe Leu Ser Glu Ala Thr Ala Thr Leu Ala Gly Ala Gly
        260                 265                 270

Phe Thr Glu Glu Lys Asp His Leu Glu Trp Asp Leu Thr Val Ser Lys
        275                 280                 285

Pro Leu Asn Val Glu Leu Pro Arg Ser Met Val Glu Val Val Thr Ser
        290                 295                 300

Trp Asn Leu Pro Met Ser Tyr Trp Leu Asn Asn Tyr Val Phe Lys Asn
305                 310                 315                 320

Ala Leu Arg Leu Gly Thr Phe Ser Ala Val Leu Val Thr Tyr Ala Ala
                325                 330                 335

Ser Ala Leu Leu His Gly Phe Ser Phe His Leu Ala Ala Val Leu Leu
                340                 345                 350

Ser Leu Ala Phe Ile Thr Tyr Val Glu His Val Leu Arg Lys Arg Leu
                355                 360                 365

Ala Arg Ile Leu Ser Ala Cys Val Leu Ser Lys Arg Cys Pro Pro Asp
            370                 375                 380

Cys Ser His Gln His Arg Leu Gly Leu Gly Val Arg Ala Leu Asn Leu
385                 390                 395                 400

Leu Phe Gly Ala Leu Ala Ile Phe His Leu Ala Tyr Leu Gly Ser Leu
                405                 410                 415

Phe Asp Val Asp Val Asp Asp Thr Thr Glu Glu Gln Gly Tyr Gly Met
            420                 425                 430

Ala Tyr Thr Val His Lys Trp Ser Glu Leu Ser Trp Ala Ser His Trp
            435                 440                 445

Val Thr Phe Gly Cys Trp Ile Phe Tyr Arg Leu Ile Gly
        450                 455                 460

<210> SEQ ID NO 2
<211> LENGTH: 1386
<212> TYPE: DNA
<213> ORGANISM: human

<400> SEQUENCE: 2
atggccacct ttagccgcca ggaattttc  cagcagctac tgcaaggctg tctcctgcct      60
actgcccagc agggccttga ccagatctgg ctgctccttg ccatctgcct cgcctgccgc     120
ctcctctgga ggctcgggtt gccatcctac ctgaagcatg caagcaccgt ggcaggcggg     180
ttcttcagcc tctaccactt cttccagctg cacatggttt gggtcgtgct gctcagcctc     240
ctgtgctacc tcgtgctgtt cctctgccga cattcctccc atcgaggcgt cttcctatcc     300
gtcaccatcc tcatctacct actcatgggt gagatgcaca tggtagacac cgtgacatgg     360
cacaagatgc gagggcaca  gatgattgtg ccatgaagg  cagtgtctct gggcttcgac     420
ctggaccggg cgaggtgggg tacgtgcccc tcgccagtgg agttcatggg ctacctctac     480
ttcgtgggca ccatcgtctt cgggccctgg atatccttcc acagctacct acaaactgtc     540
caaggccgcc cactgagctg ccggtggctg cagaaggtgg cccggagcct ggcactggcc     600
ctgctgtgcc ttgtgctgtc cacttgcgtg ggcccctacc tcttcccgta cttcatcccc     660
ctcaacggtg accgcctcct cgcaacaag  aaacgcaaag ccaggggcac catggtaagg     720
tggctgcgag cctacgagag tgctgtctcc ttccacttca gcaactattt tgtgggcttt     780
ctttccgagg ccacgccac  gttggcgggg ctggctttta ccgaggagaa ggatcacctg     840
gaatgggacc tgacggtgtc caagccactg aatgtggagc tgcctcggtc aatggtggaa     900
```

-continued

```
gttgtcacaa gctggaacct gcccatgtct tattggctaa ataactatgt tttcaagaat      960
gctctccgcc tggggacctt ctcggctgtg ctggtcacct atgcagccag cgccctccta     1020
catggcttca gtttccacct ggctgcggtc ctgctgtccc tggcttttat cacttacgtg     1080
gagcatgtcc tccggaagcg cctggctcgg atcctcagtg cctgtgtctt gtcaaagcgg     1140
tgcccgccag actgttcgca ccagcatcgc ttgggcctgg gggtgcgagc cttaaacttg     1200
ctctttggag ctctggccat cttccacctg gcctacctgg gctccctgtt tgatgtcgat     1260
gtggatgaca ccacagagga gcagggctac ggcatggcat acactgtcca caagtggtca     1320
gagctcagct gggccagtca ctgggtcact tttggatgct ggatcttcta ccgtctcata     1380
ggctga                                                               1386

<210> SEQ ID NO 3
<211> LENGTH: 20
<212> TYPE: DNA
<213> ORGANISM: human

<400> SEQUENCE: 3
tacctgaagc atgcaagcac                                                   20

<210> SEQ ID NO 4
<211> LENGTH: 20
<212> TYPE: DNA
<213> ORGANISM: human

<400> SEQUENCE: 4
cggtgtctac catgtgcatc                                                   20

<210> SEQ ID NO 5
<211> LENGTH: 20
<212> TYPE: DNA
<213> ORGANISM: human

<400> SEQUENCE: 5
tcctcagtgc ctgtgtcttg                                                   20

<210> SEQ ID NO 6
<211> LENGTH: 20
<212> TYPE: DNA
<213> ORGANISM: human

<400> SEQUENCE: 6
gcatccaaaa gtgacccagt                                                   20

<210> SEQ ID NO 7
<211> LENGTH: 20
<212> TYPE: DNA
<213> ORGANISM: human

<400> SEQUENCE: 7
ctcggtcaat ggtggaagtt                                                   20

<210> SEQ ID NO 8
<211> LENGTH: 20
<212> TYPE: DNA
<213> ORGANISM: human

<400> SEQUENCE: 8
caagacacag gcactgagga                                                   20
```

```
<210> SEQ ID NO 9
<211> LENGTH: 20
<212> TYPE: DNA
<213> ORGANISM: human

<400> SEQUENCE: 9
tgcctgtgtc ttgtcaaagc                                               20

<210> SEQ ID NO 10
<211> LENGTH: 20
<212> TYPE: DNA
<213> ORGANISM: human

<400> SEQUENCE: 10
gcatccaaaa gtgacccagt                                               20

<210> SEQ ID NO 11
<211> LENGTH: 20
<212> TYPE: DNA
<213> ORGANISM: human

<400> SEQUENCE: 11
ctcggtcaat ggtggaagtt                                               20

<210> SEQ ID NO 12
<211> LENGTH: 20
<212> TYPE: DNA
<213> ORGANISM: human

<400> SEQUENCE: 12
ggtggaaact gaagccatgt                                               20

<210> SEQ ID NO 13
<211> LENGTH: 21
<212> TYPE: DNA
<213> ORGANISM: human

<400> SEQUENCE: 13
aagttgtcac aagctggaac c                                             21

<210> SEQ ID NO 14
<211> LENGTH: 21
<212> TYPE: DNA
<213> ORGANISM: human

<400> SEQUENCE: 14
aacaagaaac gcaaagccag g                                             21
```